(12) United States Patent
Zhou et al.

(10) Patent No.: US 10,759,797 B2
(45) Date of Patent: Sep. 1, 2020

(54) PHARMACEUTICALLY ACCEPTABLE SALT OF EGFR INHIBITOR, CRYSTAL FORM THEREOF, PREPARATION METHOD THEREFOR AND APPLICATION THEREOF

(71) Applicant: Wuxi Shuangliang Biotechnology Co., Ltd., Jiangyin, Jiangsu (CN)

(72) Inventors: Ping Zhou, Jiangsu (CN); Jiaquan Wu, Wayland, MA (US); Shenshuang Jin, Jiangsu (CN); Li Li, Jiangsu (CN)

(73) Assignee: Wuxi Shuangliang Biotechnology Co., Ltd., Jiangsu (CN)

( * ) Notice: Subject to any disclaimer, the term of this patent is extended or adjusted under 35 U.S.C. 154(b) by 0 days.

(21) Appl. No.: 16/329,544

(22) PCT Filed: Jan. 2, 2018

(86) PCT No.: PCT/CN2018/070011
§ 371 (c)(1),
(2) Date: Feb. 28, 2019

(87) PCT Pub. No.: WO2018/218963
PCT Pub. Date: Dec. 6, 2018

(65) Prior Publication Data
US 2019/0194199 A1 Jun. 27, 2019

(30) Foreign Application Priority Data
Jun. 2, 2017 (CN) .......................... 2017 1 0408362

(51) Int. Cl.
*C07D 471/04* (2006.01)
*C07D 403/04* (2006.01)
*C07D 403/02* (2006.01)
*A61P 35/00* (2006.01)

(52) U.S. Cl.
CPC ............ *C07D 471/04* (2013.01); *A61P 35/00* (2018.01); *C07D 403/02* (2013.01); *C07D 403/04* (2013.01); *C07B 2200/13* (2013.01)

(58) Field of Classification Search
None
See application file for complete search history.

(56) References Cited

U.S. PATENT DOCUMENTS

2016/0324854 A1* 11/2016 Finnie .................. A61K 9/2054
2018/0208585 A1* 7/2018 Wu ....................... A61K 31/403

FOREIGN PATENT DOCUMENTS

| CN | 104961731 A | 10/2015 |
| CN | 105294717 | 2/2016 |
| CN | 106132957 A | 11/2016 |
| CN | 106432231 | 2/2017 |
| JP | 2013512956 | 4/2013 |
| JP | 2013544273 | 12/2013 |
| WO | WO 2011071821 | 6/2011 |
| WO | WO 2013014448 | 1/2013 |
| WO | WO-2017035753 A1 * 3/2017 | .......... A61K 31/403 |

OTHER PUBLICATIONS

Zhou et al., "Design, synthesis and evaluation of the osimertinib analogue (C-005) as potent EGFR inhibitor against NSCLC", Bioorg. Med. Chem., 2018, vol. 26, pp. 6135-6145 (Year: 2018).*
Yver, "Osimertinib (AZD9291)—a science driven, collaborative approach to rapid drug design and development", Annals of Oncology, 2016, vol. 27, pp. 1165-1170 (Year: 2016).*
Yates et al., "Irreversible Inhibition of EGFR: Modeling the Combined Pharmacokinetic-Pharmacodynamic Relationship of Osimertinib and Its Active Metabolite AZ5104", Mol. Cancer Ther., 2016, vol. 15, No. 10, pp. 2378-2387 (Year: 2016).*
Ward et al., "Structure- and Reactivity-Based Development of Covalent Inhibitors of the Activating and Gatekeeper Mutant Forms of the Epidermal Growth Factor Receptor (EGFR)", J. Med. Chem., 2013, vol. 56, pp. 7025-7048 (Year: 2013).*
Pires et al., Org. Lett., 2016, vol. 18, pp. 3250-3253 (Year: 2016).*
Merour et al., Molecules, 2014, vol. 19, pp. 19935-19979 (Year: 2014).*
Finlay et al., J. Med. Chem., 2014, vol. 57, No. 20, pp. 8249-8267 (Year: 2014).*
Jieying Luo, et al., "Theory and Practice of Pharmacy in Modern Physics", Shanghai Scientific & Technical Publishers, Apr. 30, 2005, pp. 293-295, with English translation.
JP Office Action in Japanese Appln. No. 2019-515244, dated Feb. 4, 2020, 4 pages (English translation).

(Continued)

*Primary Examiner* — James D. Anderson
*Assistant Examiner* — Stephanie K Springer
(74) *Attorney, Agent, or Firm* — Fish & Richardson P.C.

(57) ABSTRACT

Provided in the present disclosure are a pharmaceutically acceptable salt of an epidermal growth factor receptor (EGFR) inhibitor, a crystal form thereof, a preparation method therefor and an application thereof. The structural formula of the EGFR inhibitor is as shown in formula I, and the pharmaceutically acceptable salt is a mesylate, p-toluenesulfonate, phosphate, hydrochloride or citrate salt of the EGFR inhibitor. The pharmaceutically acceptable salt of EGFR inhibitor of the present disclosure has a specific crystal form, has a higher solubility and stability than a corresponding free base, is more suitable for preparing drugs for use in treating cancer (especially non-small cell lung cancer), and satisfies the requirements for bioavailability and drug efficacy.

Formula I

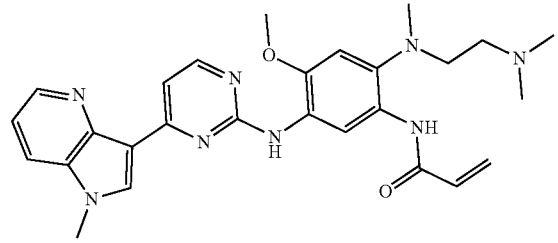

15 Claims, 14 Drawing Sheets

(56) References Cited

OTHER PUBLICATIONS

European Search Report dated May 27, 2020 in corresponding European Application No. EP 18810477.2.
Rolf Hilfiker, et al., "Relevance of Solid-State Properties for Pharmaceutical Products", Jan. 1, 2006, Jan. 1, 2006, pp. 1-19, XP002525043.
P. Heinrich Stahl, et al., "Tables of Salt-Forming Acids and Bases" 1-15 in: "Handbook of Pharmaceutical Salts—Properties, Selection, and Use", Jan. 1, 2002, Verlag Helvetica Chimica Acta; Wiley-VCH, Zurich, Weinheim, XP55247250.
Richard J Bastin, et al., "Salt Selection 1-15 and Optimisation Procedures for Pharmaceutical New Chemical Entities", Organic Process Research and Development, American Chemical Society, US, vol. 4, No. 5, Jul. 19, 2000, pp. 427-435, XP008154792.
Mino R. Caira, et al., "Crystalline Polymorphism of Organic Compounds", Topics in Current Chemistry; Springer, Berlin, DE, vol. 198, Jan. 1, 1998, pp. 163-208, XP001156954.

\* cited by examiner

PHARMACEUTICALLY ACCEPTABLE SALT OF EGFR INHIBITOR, CRYSTAL FORM THEREOF, PREPARATION METHOD THEREFOR AND APPLICATION THEREOF

TECHNICAL FIELD

The present disclosure belongs to the technical field of medicine, and relates to a pharmaceutically acceptable salt of EGFR inhibitor, a crystal form thereof, a preparation method therefor, and application thereof.

BACKGROUND

For patients suffering from late phase non-small cell lung cancer (NSCLC), targeted therapies against epidermal growth factor receptor (EGFR) and anaplastic lymphoma kinase (ALK) mutations are standard treatment regimens today. However, the duration of efficacy of these drugs is generally very short, with resistance occurring within 9 to 11 months, due to the ability of cancer cells to evade the therapeutic activity of EGFR or ALK inhibitors by mutation and altered growth patterns. It has been reported that for Asian patients with late phase non-small cell lung cancer, 50% of the acquired resistance to anti-EGFR treatments is caused by T790M mutation.

In order to overcome the related drug resistance caused by T790M mutation, some irreversible ATP competitive inhibitors (such as HMPL-813, CI-1033, HKI-272, HS-10182) have entered the clinical research phase. The structure of the irreversible inhibitor contains a receptor fragment that may undergo Michael addition reaction, which is capable of generating a covalent bond with a thiol group (SH) in a conserved amino acid residue (Cys797) of the receptor binding site. The binding ability of such inhibitors to EGFR via irreversible covalent bonds is generally stronger than the binding ability of the reversible inhibitors to EGFR (see Journal of Medicinal Chemistry, 2009, 52:1231-1236). Nevertheless, the clinical trial results of the above irreversible inhibitors indicate that these inhibitors still have certain limitations, such as toxic effects due to off-target effects, and failure to achieve sufficient drug concentration in patients due to side effects caused by low selectivity. Therefore, the development of a new type of irreversible EGFR inhibitor has a great clinical significance and application prospect.

AZD9291, developed and marketed by AstraZeneca, is the first third-generation oral, irreversible, selective EGFR mutation inhibitor that may be used for both activated and resistant mutant EGFR, that is, AZD9291 may make the drug resistance caused by T790M mutation ineffective. AZD9291 has a relatively good therapeutic effect on NSCLC patients who have resistance to epidermal growth factor receptor tyrosine kinase inhibitor (EGFR-TKI) and have T7901M mutation. The structure of AZD9291 is disclosed in Chinese patent application CN103702990A, which also discloses the polymorph of AZD9291 and its pharmaceutically acceptable form mesylate salt.

Since the third generation EGFR inhibitor has unique efficacy and AZD9291 is the only product in the market, competition for new drugs is very fierce. Chinese patent application CN106132957A discloses a series of 2-arylamine pyridine, pyrimidine or triazine deriviatives, which were structurally characterized. In addition, this application also conducted activity tests for the above compounds at cellular level. The results show that these compounds have high EGFR inhibitory activity, while have relatively low inhibitory activity towards wild type EGFR, thus may be developed into novel anti-tumor drugs. However, the above application lacks research and protection of the pharmaceutically acceptable form (for example, a salt-based crystal form) of the crude drug, and needs further development and improvement.

SUMMARY

Problems to be Solved by the Disclosure

In order to investigate the relationship between the specific pharmaceutically acceptable forms of EGFR inhibitor crude drug and the physicochemical properties thereof, and to develop a specific pharmaceutically acceptable form of EGFR inhibitor that is more suitable for patent medicine, the present disclosure provides a pharmaceutically acceptable salt of EGFR inhibitor, a crystal form thereof, a preparation method therefor, and application thereof.

Solution for Solving the Problems

The present disclosure provides a pharmaceutically acceptable salt of EGFR inhibitor, which is a salt formed by an EGFR inhibitor and an acid, the EGFR inhibitor has the structure as shown in formula I,

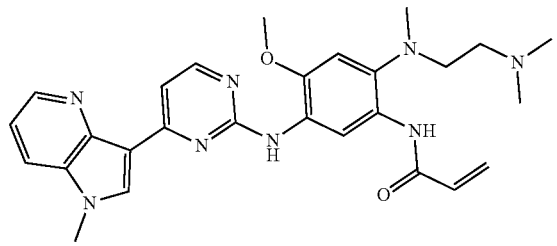

formula I and the acid is methanesulfonic acid, p-toluenesulfonic acid, phosphoric acid, hydrogen chloride, or citric acid.

The present disclosure provides the pharmaceutically acceptable salt of EGFR inhibitor, the mesylate salt of the EGFR inhibitor has a crystal form A, and the X-ray powder diffraction pattern of the crystal form A has characteristic peaks at 2θ values of 6.8°±0.2°, 14.0°±0.2°, and 21.6°±0.2°.

Further, the X-ray powder diffraction pattern of the crystal form A has characteristic peaks at at least one of 2θ values of 13.5°±0.2°, 15.6°±0.2°, 18.1°±0.2°, and 24.0°±0.2°.

Further, the X-ray powder diffraction pattern of the crystal form A has characteristic peaks at at least one of 2θ values of 5.8°±0.2°, 11.5°±0.2°, 12.0°±0.2°, 14.8°±0.2°, 17.2°±0.2°, 17.5°±0.2°, 18.6°±0.2°, 19.0°±0.2°, 22.2°±0.2°, 24.6°±0.2°, 27.2°±0.2°, and 27.7°±0.2°.

The present disclosure provides the pharmaceutically acceptable salt of EGFR inhibitor, the p-toluenesulfonate salt of the EGFR inhibitor has a crystal form B, and the X-ray powder diffraction pattern of the crystal form B has characteristic peaks at 2θ values of 10.6°±0.2°. 15.1°±0.2°, 18.1°±0.2°, 22.4°±0.2°, and 24.8°±0.2°.

Further, the X-ray powder diffraction pattern of the crystal form B has characteristic peaks at at least one of 2θ values of 7.8°±0.2°, 10.2°±0.2°, 12.9°±0.2°, 18.7°±0.2°, 21.0°±0.2°, 21.4°±0.2°, and 23.7°±0.2°.

Further, the X-ray powder diffraction pattern of the crystal form B has characteristic peaks at at least one of 2θ values of 11.2°±0.2°, 11.7°±0.2° 14.2°±0.2°, 16.1°±0.2°, 16.5°±0.2°, 19.7°±0.2°, 23.2°±0.2°, 24.3°±0.2°, 26.9°±0.2°, 28.0°±0.2°, and 29.5°±0.2°.

The present disclosure provides the pharmaceutically acceptable salt of EGFR inhibitor, the phosphate salt of the EGFR inhibitor has a crystal form C, and the X-ray powder diffraction pattern of the crystal form C has characteristic peaks at 2θ values of 14.1°±0.2° 16.0°±0.2°, and 25.3°±0.2°.

Further, the X-ray powder diffraction pattern of the crystal form C has characteristic peaks at 2θ values of 8.9°±0.2°, 19.9°±0.2°, and 22.7°±0.2°.

Further, the X-ray powder diffraction pattern of the crystal form C has characteristic peaks at at least one of 2θ values of 11.2°±0.2°, 11.9°±0.2°, 12.6°±0.2°, 16.8°±0.2°, 17.8°±0.2°, 20.5°±0.2°, 21.4°±0.2°, 22.1°±0.2°, 23.2°±0.2°, 23.8°±0.2°, 24.5°±0.2°, 26.0°±0.2°, and 28.2°±0.2°.

The present disclosure provides the pharmaceutically acceptable salt of EGFR inhibitor, the hydrochloride salt of the EGFR inhibitor has a crystal form D, and the X-ray powder diffraction pattern of the crystal form D has characteristic peaks at 2θ values of 7.8°±0.2°, 9.8°±0.2°, 16.2°±0.2°, 21.3°±0.2°, 26.3°±0.2°, and 27.6°±0.2°.

Further, the X-ray powder diffraction pattern of the crystal form D has characteristic peaks at at least one of 2θ values of 16.0°±0.2°, 17.1°±0.2°, 18.2°±0.2°, 21.9°±0.2°, 22.5°±0.2°, 24.6°±0.2°, and 25.8°±0.2°.

Further, the X-ray powder diffraction pattern of the crystal form D has characteristic peaks at at least one of 2θ values of 13.8°±0.2°, 14.5°±0.2°, 15.5°±0.2°, 16.7°±0.2°, 20.5°±0.2°, and 23.5°±0.2°.

The present disclosure provides the pharmaceutically acceptable salt of EGFR inhibitor, the citrate salt of the EGFR inhibitor has a crystal form E, and the X-ray powder diffraction pattern of the crystal form E has characteristic peaks at 2θ values of 5.4°±0.2°, 12.0°±0.2°, and 21.2°±0.2°.

Further, the X-ray powder diffraction pattern of the crystal form E has characteristic peaks at at least one of 2θ values of 10.8°±0.2°, 17.5°±0.2°, 24.9°±0.2°, and 25.4°±0.2°.

Further, the X-ray powder diffraction pattern of the crystal form E has characteristic peaks at at least one of 2θ values of 9.0°±0.2°, 12.4°±0.2°, 13.3°±0.2°, 16.0°±0.2°, and 20.4°±0.2°.

The present disclosure provides the pharmaceutically acceptable salt of EGFR inhibitor, the pharmaceutically acceptable salt is an amorphous phosphate salt, and has the characteristic peaks of X-ray powder diffraction spectrum as shown in FIG. 7.

The present disclosure also provides a preparation method of the crystal form of the pharmaceutically acceptable salt of EGFR inhibitor, which comprises:

adding the EGFR inhibitor and the acid into an alcoholic solvent or water to form a salt; adding a ketonic solvent to devitrify and obtain the crystal form of the pharmaceutically acceptable salt of EGFR inhibitor.

Preferably, the alcoholic solvent has a carbon number of 1 to 6, and the ketonic solvent has a carbon number of 3 to 6.

The present disclosure also provides use of the pharmaceutically acceptable salt of EGFR inhibitor in preparation of a drug for treating cancer, and preferably in preparation of a drug for treating non-small cell lung cancer.

The present disclosure also provides an amorphous EGFR inhibitor phosphate salt, which is a salt formed by an EGFR inhibitor represented by formula I and phosphoric acid, and has the characteristic peaks of X-ray powder diffraction spectrum as shown in FIG. 7; and use of the amorphous EGFR inhibitor phosphate salt in preparation of a drug for treating cancer, preferably in preparation of a drug for treating non-small cell lung cancer.

Effects of the Disclosure

The present disclosure provides a mesylate, p-toluenesulfonate, phosphate, hydrochloride or citrate salt of an EGFR inhibitor (N-(2-((2-(dimethylamino)ethyl)(methyl)amino)-4-methoxy-5-((4-(1-methyl-1H-pyrrolo[2,3-b]pyridin-3-yl)pyrimidin-2-yl)amino)phenyl)acrylamide). Based on specific crystal forms, these pharmaceutically acceptable salts have higher solubility and stability than corresponding free bases, are more suitable for drug development, and satisfy the requirements for bioavailability and drug efficacy.

In addition, as compared with the free base form of the EGFR inhibitor, the pharmaceutically acceptable salt (mesylate, p-toluenesulfonate, phosphate, hydrochloride, or citrate salt) of EGFR inhibitor provided by the present disclosure is sandy or granular, which is more convenient for subsequent formulation processing operations.

DETAILED DESCRIPTION

Figure 1:
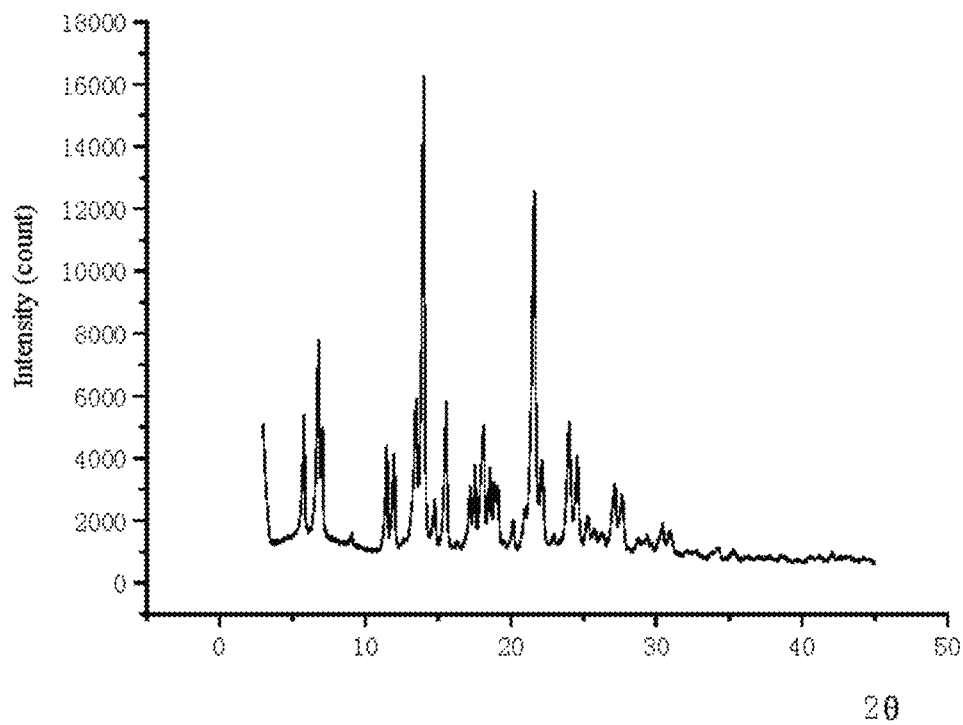
FIG. 1 is a XRPD pattern of an EGFR inhibitor mesylate salt present in the form of a crystal form A.

The present disclosure provides a pharmaceutically acceptable salt of EGFR inhibitor, and the structure of the EGFR inhibitor is shown in formula I (chemical name: N-(2-((2-(dimethylamino)ethyl)(methyl)amino)-4-methoxy-5-(4-(1-methyl-1H-pyrrolo[3,2-b]pyridin-3-yl)pyrimidin-2-yl)amino)phenyl)acrylamide):

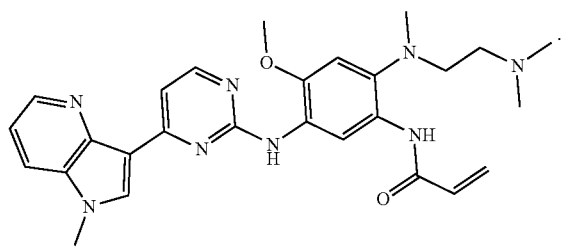

formula I

The pharmaceutically acceptable salt includes mesylate, p-toluenesulfonate, phosphate, hydrochloride or citrate salt.

Unless otherwise stated, the EGFR inhibitor in the present disclosure refers to the above compound.

The present disclosure further provides a crystal form of the pharmaceutically acceptable salt of EGFR inhibitor.

When the pharmaceutically acceptable salt is a mesylate salt, the crystal form is a crystal form A. In one specific embodiment of the present disclosure, the X-ray powder diffraction pattern of the crystal form A has characteristic peaks at 2θ values of 5.8°±0.2°, 6.8°±0.2°, 11.5°±0.2°, 12.0°±0.2°, 13.5°±0.2°, 14.0°±0.2°, 14.8°±0.2°, 15.6°±0.2°, 17.2°±0.2°, 17.5°±0.2°, 18.1°±0.2°, 18.6°±0.2°, 19.0°±0.2°, 21.6°±0.2°, 22.2°±0.2°, 24.0°±0.2°, 24.6°±0.2°, 27.2°±0.2°, and 27.7°±0.2°; further, the X-ray powder diffraction pattern of the crystal form A is substantially consistent with FIG. 1; more further, in a specific embodiment of the present disclosure, the differential scanning calorimetry thermogram of the crystal form A is substantially consistent with FIG. 2.

When the pharmaceutically acceptable salt is a p-toluenesulfonate salt, the crystal form is a crystal form B. In one specific embodiment of the present disclosure, the X-ray powder diffraction pattern of the crystal form B has characteristic peaks at 2θ values of 7.8°±0.2°, 10.2°±0.2°, 10.6°±0.2°, 11.2°±0.2°, 11.7°±0.2°, 12.9°±0.2°, 14.2°±0.2°, 15.1°±0.2°, 16.1°±0.2°, 16.5°±0.2°, 18.1°±0.2°, 18.7°±0.2°, 19.7°±0.2°, 21.0°±0.2°, 21.4°±0.2°, 22.4°±0.2°, 23.2°±0.2°, 23.7°±0.2°, 24.3°±0.2°, 24.8°±0.2°, 26.9°±0.2°, 28.0°±0.2°, and 29.5°±0.2°; further, the X-ray powder diffraction pattern of the crystal form B is substantially consistent with FIG. 3; more further, the differential scanning calorimetry thermogram of the crystal form B is substantially consistent with FIG. 4.

When the pharmaceutically acceptable salt is a phosphate salt, the crystal form is a crystal form C. In one specific embodiment of the present disclosure, the X-ray powder diffraction pattern of the crystal form C has characteristic peaks at 2θ values of 8.9°±0.2°, 11.2°±0.2°, 11.9°±0.2°, 12.6°±0.2°, 14.1°±0.2°, 16.0°±0.2°, 16.8°±0.2°, 17.8°±0.2°, 19.9°±0.2°, 20.5°±0.2°, 21.4°±0.2°, 22.1°±0.2°, 22.7°±0.2°, 23.2°±0.2°, 23.8°±0.2°, 24.5°±0.2°, 25.3°±0.2°, 26.0°±0.2°, and 28.2°±0.2°; further, the X-ray powder diffraction pattern of the crystal form C is substantially consistent with FIG. 5; more further, the differential scanning calorimetry thermogram of the crystal form C is substantially consistent with FIG. 6.

When the pharmaceutically acceptable salt is a hydrochloride salt, the crystal form is a crystal form D. In one specific embodiment of the present disclosure, the X-ray powder diffraction pattern of the crystal form D has characteristic peaks at 2θ values of 7.8°±0.2°, 9.8°±0.2°, 13.8°±0.2°, 14.5°±0.2°, 15.5°±0.2°, 16.0°±0.2°, 16.2°±0.2°, 16.7°±0.2°, 17.1°±0.2°, 18.2°±0.2°, 20.5°±0.2°, 21.3°±0.2°, 21.9°±0.2°, 22.5°±0.2°, 23.5°±0.2°, 24.6°±0.2°, 25.8°±0.2°, 26.3°±0.2°, and 27.6°±0.2°; further, the X-ray powder diffraction pattern of the crystal form D is substantially consistent with FIG. 8; more further, the differential scanning calorimetry thermogram of the crystal form D is substantially consistent with FIG. 9.

Figure 10:
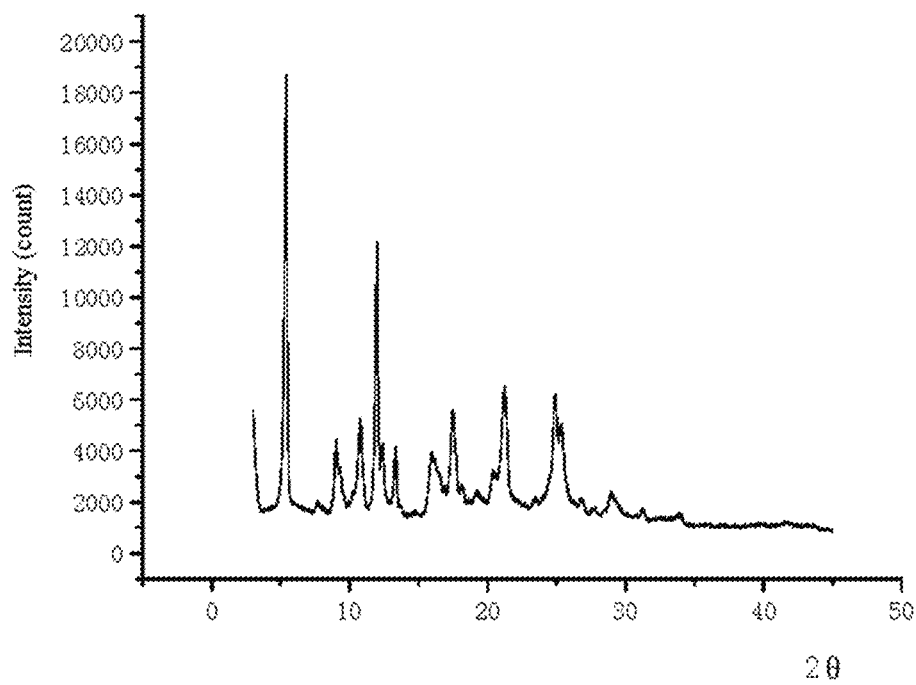
FIG. 10 is a XRPD pattern of an EGFR inhibitor citrate salt present in the form of a crystal form E.
Figure 11:
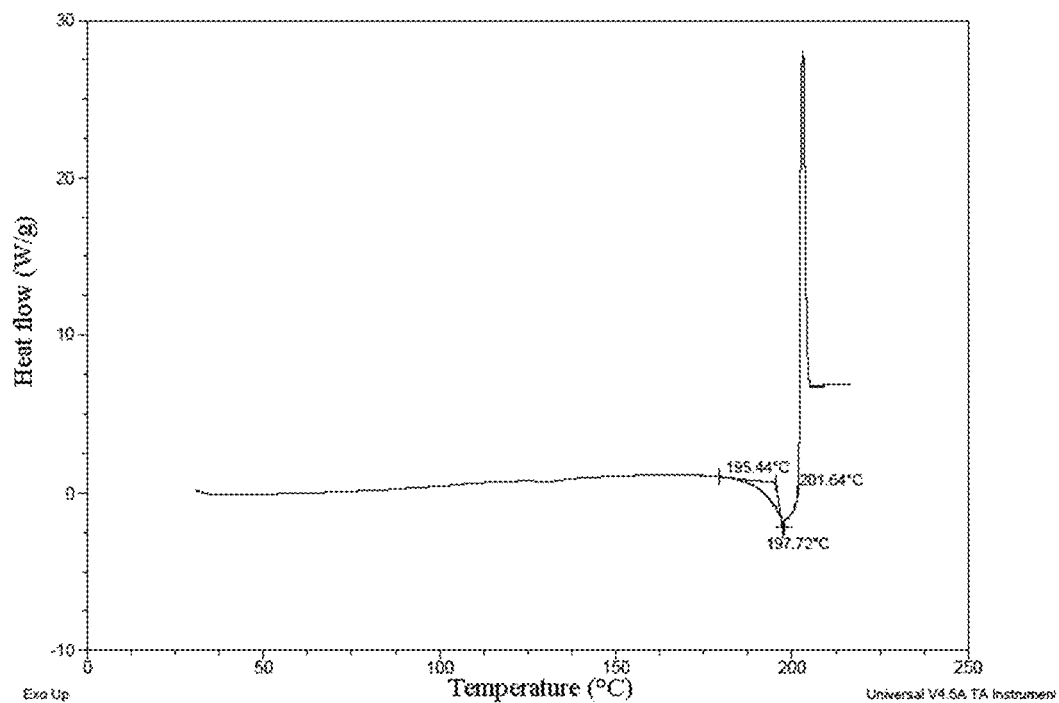
FIG. 11 is a DSC plot of the EGFR inhibitor citrate salt present in the form of the crystal form E.

When the pharmaceutically acceptable salt is a citrate salt, the crystal form is a crystal form E, the X-ray powder diffraction pattern of the crystal form E has characteristic peaks at 2θ values of 5.4°±0.2°, 9.0°±0.2°, 10.8°±0.2°, 12.0°±0.2°, 12.4°±0.2°, 13.3°±0.2°, 16.0°±0.2°, 17.5°±0.2°, 20.4°±0.2°, 21.2°±0.2°, 24.9°±0.2°, and 25.4°±0.2°, further, the X-ray powder diffraction pattern of the crystal form E is substantially consistent with FIG. 10; more further, the differential scanning calorimetry thermogram of the crystal form E is substantially consistent with FIG. 11.

The preparation method of the crystal form of the pharmaceutically acceptable salt of EGFR inhibitor comprises:

adding the EGFR inhibitor present in a free base form and an acid into an alcoholic solvent or water to form a salt, then adding (preferably dropwise) a ketonic solvent to denitrify and obtain the crystal form of the pharmaceutically acceptable salt of EGFR inhibitor. The EGFR inhibitor present in a free base form and the acid preferably form a salt equimolarly.

Preferably, the alcoholic solvent has a carbon number of 1 to 6; more preferably, the alcoholic solvent is methanol or ethanol.

Preferably, in the preparation method described above, the usage amount ratio of the alcoholic solvent to the EGFR inhibitor is 2 to 5 ml: 1 g, preferably 3 ml: 1 g.

Preferably, in the preparation method described above, the ketonic solvent has a carbon number of 3 to 6; more preferably, the ketonic solvent is acetone.

Preferably, in the preparation method described above, the usage amount ratio of the ketonic solvent to the EGFR inhibitor is 10 to 30 ml: 1 g, preferably 20 ml: 1 g.

The preparation method of the EGFR inhibitor phosphate salt (amorphous) comprises forming a salt by the EGFR inhibitor present in a free base form and phosphoric acid, then adding a ketonic solvent so that the solid precipitates.

The EGFR inhibitor present in a free base form and phosphoric acid preferably form a salt equimolarly. Preferably, in the preparation method described above, the ketonic solvent has a carbon number of 3 to 6; more preferably, the ketonic solvent is acetone.

In a specific embodiment of the present disclosure, the technical solution of the present disclosure will be further explained below in conjunction with the drawings and specific examples. It is to be understood that the following examples are for illustration and explanation of the present disclosure only, and are not for limitation of the scope of protection of the present disclosure.

The abbreviations referred to in the present disclosure have the following meanings:

XRPD: X-ray powder diffraction;
DSC: differential scanning calorimetry;
$^1$H-NMR: hydrogen nuclear magnetic resonance spectrum;
LC-MS: liquid chromatography-mass spectrometry.

Figure 18:
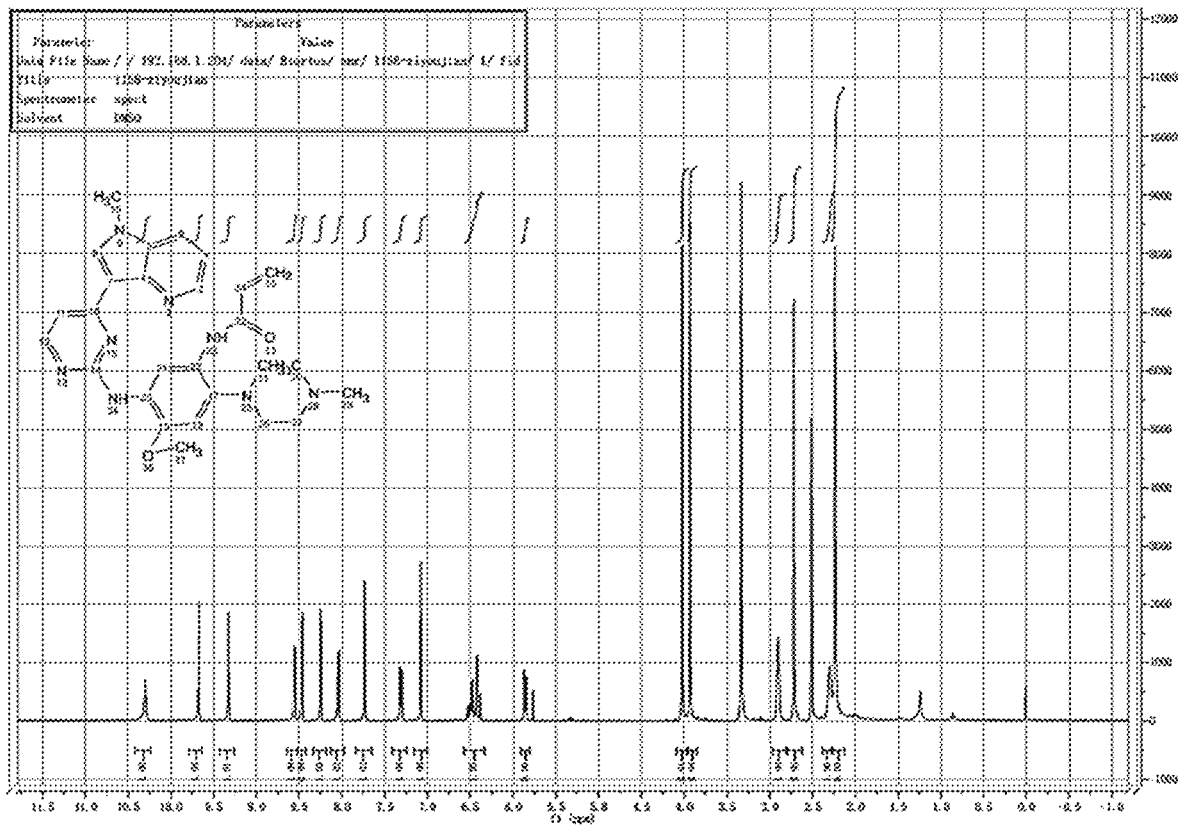
FIG. 18 is a $^1$H-NMR spectrum of the EGFR inhibitor present in a free base form.
Figure 19:
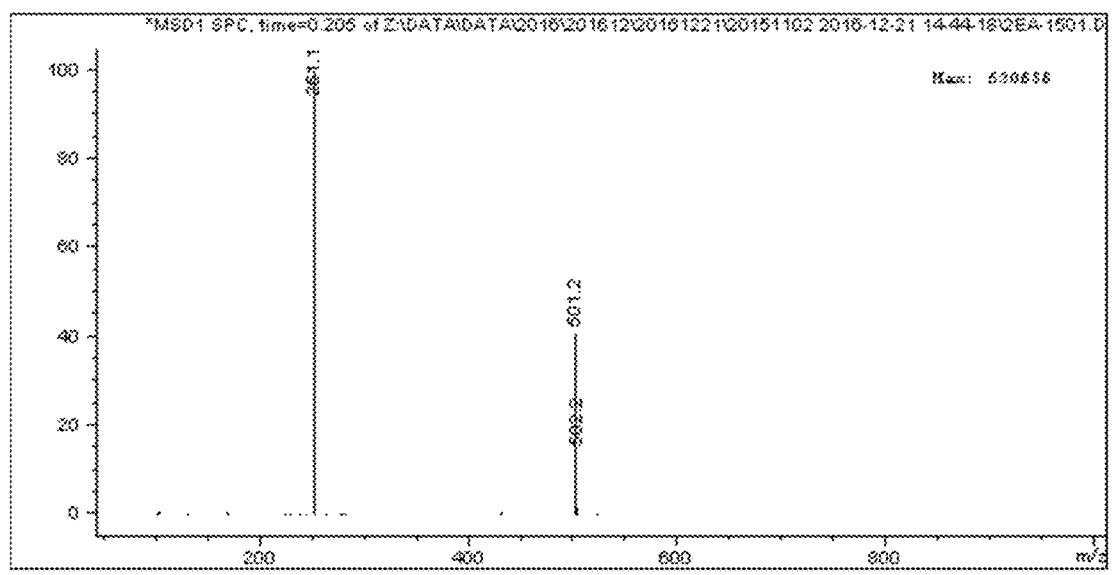
FIG. 19 is a mass spectrogram of the EGFR inhibitor present in a free base form.

The EGFR inhibitor used in the following examples is self-made, has a purity of 99.7% and an appearance of a light yellow granular solid. For the preparation method of the EGFR inhibitor, refer to Chinese patent application CN106132957A. The structure confirmation data is as follows:

$^1$H-NMR (400 MHz, DMSO-d$_6$): δ10.30 (1H, s), 9.67 (1H, s), 9.32 (1H, s), 8.56 to 8.54 (1H, dd), 8.47 to 8.46 (1H, d), 8.25 to 8.24 (1H, d), 8.05 to 8.03 (1H, d), 7.73 (1H, s), 7.32 to 7.29 (1H, dd), 7.08 (1H, s), 6.53 to 6.38 (2H, m), 5.87 to 5.84 (1H, dd), 4.02 (3H, s), 3.93 (3H, s), 2.92 to 2.89 (2H, t), 2.72 (3H, s), 2.30 (2H, s), 2.24 (6H, s) (as shown in FIG. 18);

ESI-MS: m/z 501.2 [M+H]$^+$, 251.2 [M+2H]$^{2+}$ (as shown in FIG. 19).

Example 1: EGFR Inhibitor Mesylate Salt (Crystal Form A)

At room temperature, the EGFR inhibitor present in a free base form (12.0 g, 24 mmol) was weighed, placed in a 500 mL flask, and 36 mL ethanol was added. Methanesulfonic acid (2.32 g, 24 mmol) was added, and was stirred at 40 to 50° C. to dissolve. Then 240 mL acetone was added dropwise, stirred at 0 to 5° C., and a grey solid precipitated. The mixture was filtered with suction, and the filter cake was rinsed with a small amount of acetone, dried using a vacuum drying oven at 60° C. to obtain a light brown solid (10.1 g, purity: 99.0%, moisture: 0.97%, melting point: 150.5 to 152.8° C.).

Figure 20:
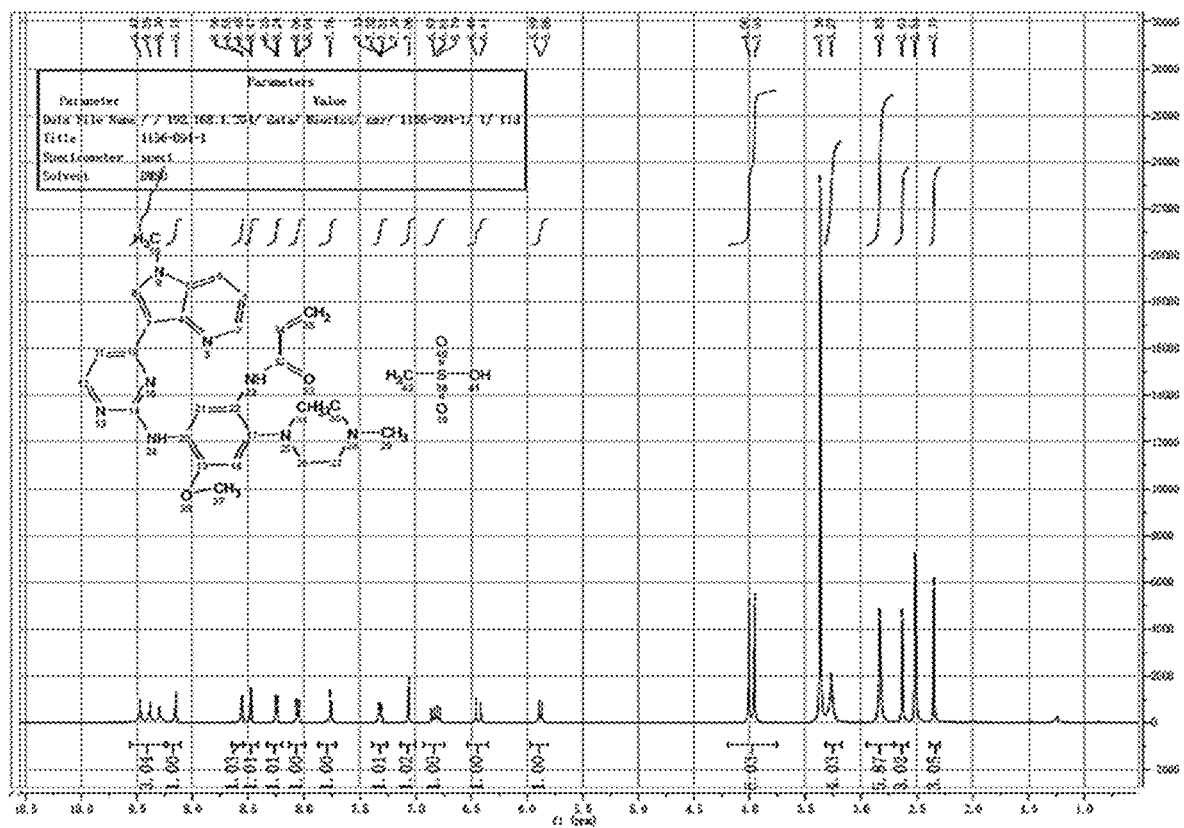
FIG. 20 is a $^1$H-NMR spectrum of the EGFR inhibitor mesylate salt present in the form of the crystal form A.

The structure confirmation data of the above product was as follows:

$^1$H-NMR (400 MHz, DMSO-d$_6$): δ9.47 (1H, s), 9.39 (1H, s), 9.30 (1H, s), 9.15 (1H, s), 8.62 (1H, s), 8.56 to 8.55 (1H, d), 8.48 to 8.47 (1H, d), 8.25 to 8.24 (1H, d), 8.06 to 8.04 (1H, d), 7.76 (1H, s), 7.33 to 7.30 (1H, m), 7.06 (1H, s), 6.83 to 6.79 (1H, dd), 6.46 to 6.41 (1H, d), 5.89 to 5.86 (1H, d), 4.00 (3H, s), 3.95 (3H, s), 3.27 (4H, m), 2.84 (6H, s), 2.64 (3H, s), 2.29 (3H, s) (as shown in FIG. 20);

ESI-MS: m/z 501.2 [M+H]$^+$, 251.2 [M+2H]$^{2+}$.

Figure 2:
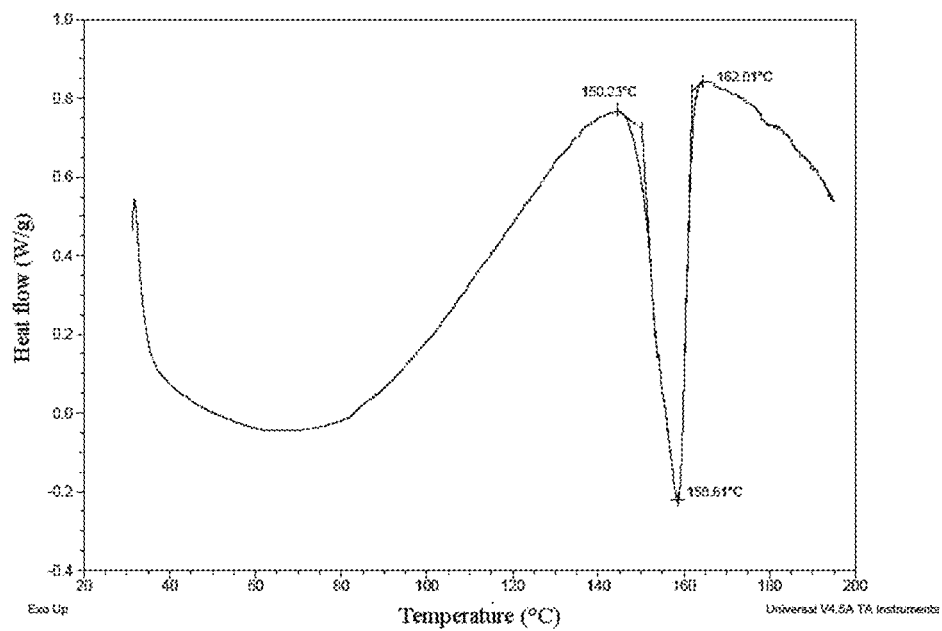
FIG. 2 is a DSC plot of the EGFR inhibitor mesylate salt present in the form of the crystal form A.

As tested, the solid obtained in the present example was an EGFR inhibitor mesylate salt, and the crystal form thereof was named as crystal form A. The XRPD data of the crystal form was as shown in Table 1, the XRPD pattern was as shown in FIG. 1, and the DSC plot was as shown in FIG. 2.

TABLE 1

XRPD data of the EGFR inhibitor mesylate salt (crystal form A)

| Serial no. | 2θ | d-spacing | Intensity (%) |
|---|---|---|---|
| 1 | 5.76 | 15.35 | 21.32 |
| 2 | 6.77 | 13.06 | 41.28 |
| 3 | 9.08 | 9.74 | 3.12 |
| 4 | 11.48 | 7.71 | 21.17 |
| 5 | 11.99 | 7.38 | 20.19 |
| 6 | 13.48 | 6.57 | 32.28 |
| 7 | 14.02 | 6.32 | 100.00 |
| 8 | 14.79 | 5.99 | 10.65 |
| 9 | 15.57 | 5.69 | 31.58 |
| 10 | 16.35 | 5.42 | 2.04 |
| 11 | 17.20 | 5.15 | 13.31 |
| 12 | 17.54 | 5.06 | 16.54 |
| 13 | 18.13 | 4.89 | 26.78 |
| 14 | 18.58 | 4.78 | 17.72 |
| 15 | 19.03 | 4.66 | 11.76 |
| 16 | 20.17 | 4.40 | 6.89 |
| 17 | 21.63 | 4.11 | 75.68 |
| 18 | 22.19 | 4.01 | 19.69 |
| 19 | 22.94 | 3.88 | 3.76 |
| 20 | 24.02 | 3.71 | 27.52 |
| 21 | 24.59 | 3.62 | 20.40 |
| 22 | 25.32 | 3.52 | 8.30 |
| 23 | 25.79 | 3.45 | 5.31 |
| 24 | 26.19 | 3.40 | 4.74 |
| 25 | 27.16 | 3.28 | 14.90 |
| 26 | 27.70 | 3.22 | 12.32 |
| 27 | 28.74 | 3.11 | 3.84 |
| 28 | 29.39 | 3.04 | 4.29 |
| 29 | 30.45 | 2.94 | 6.77 |
| 30 | 30.92 | 2.89 | 5.34 |
| 31 | 32.12 | 2.79 | 1.63 |
| 32 | 32.72 | 2.74 | 1.54 |
| 33 | 33.80 | 2.65 | 1.45 |
| 34 | 34.26 | 2.62 | 2.36 |
| 35 | 35.29 | 2.54 | 2.03 |
| 36 | 36.26 | 2.48 | 0.70 |
| 37 | 37.73 | 2.38 | 0.65 |
| 38 | 38.56 | 2.34 | 0.85 |
| 39 | 39.69 | 2.27 | 0.15 |
| 40 | 40.54 | 2.23 | 0.72 |
| 41 | 41.24 | 2.19 | 0.79 |
| 42 | 42.11 | 2.15 | 1.54 |
| 43 | 43.27 | 2.09 | 0.89 |
| 44 | 44.19 | 2.05 | 0.57 |

Example 2: EGFR Inhibitor p-Toluenesulfonate Salt (Crystal Form B)

At room temperature, the EGFR inhibitor present in a free base form (9.0 g, 18 mmol) was weighed, placed in a 500 mL flask, and 27 mL ethanol was added. P-toluenesulfonic acid monohydrate (4.56 g, 18 mmol) was added, and was stirred at 40 to 50° C. to dissolve. Then 240 mL acetone was added dropwise, and a grey solid precipitated. The mixture was filtered with suction, and the filter cake was rinsed with a small amount of acetone, oven-dried to obtain a light tan solid (10.1 g, purity: 98.7%, moisture: 0.57%, melting point: 240.1 to 243.2° C.).

Figure 21:
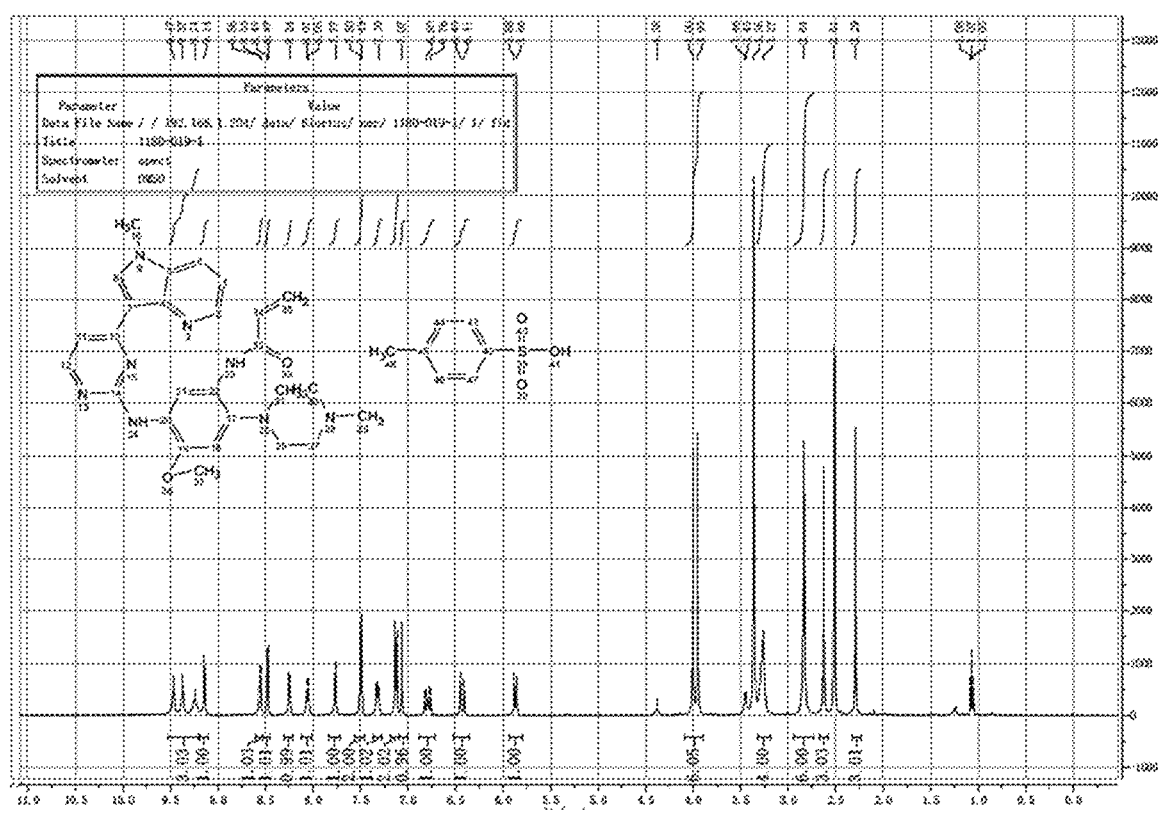
FIG. 21 is a $^1$H-NMR spectrum of the EGFR inhibitor p-toluenesulfonate salt present in the form of the crystal form B.

The structure confirmation data of the above product was as follows:

$^1$H-NMR (400 MHz, DMSO-d$_6$): δ9.47 (1H, s), 9.37 (1H, s), 9.24 (1H, s), 9.14 (1H, s), 8.56 to 8.55 (1H, d), 8.48 to 8.47 (1H, d), 8.24 to 8.23 (1H, d), 8.07 to 8.05 (1H, d), 7.77 (1H, s), 7.50 to 7.49 (2H, d), 7.30 to 7.29 (1H, m), 7.06 (1H, s), 6.80 to 6.76 (1H, dd), 6.45 to 6.41 (1H, d), 5.88 to 5.86 (1H, d), 4.00 (3H, s), 3.95 (3H, s), 3.27 (4H, m), 2.84 (3H, s), 2.64 (3H, s), 2.29 (3H, s) (as shown in FIG. 21);

ESI-MS: m/z 501.2 [M+H]$^+$, 251.2 [M+2H]$^{2+}$.

Figure 3:
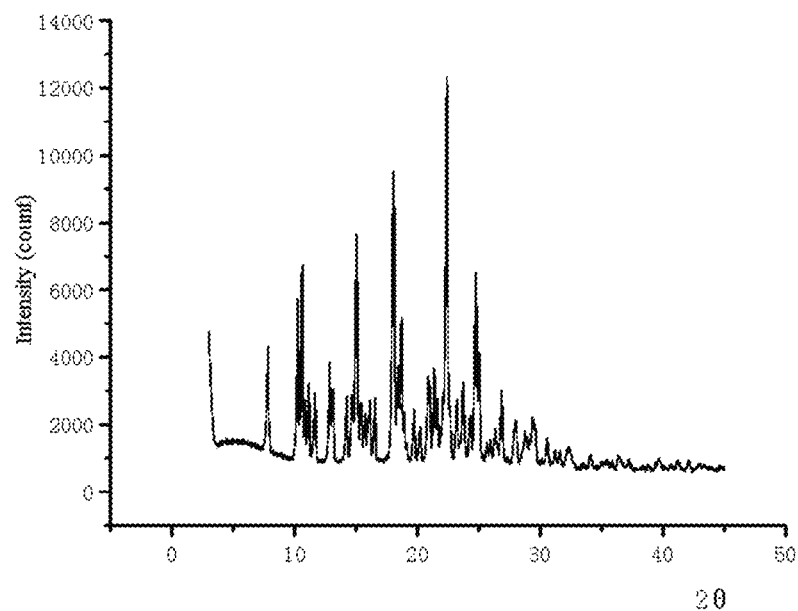
FIG. 3 is a XRPD pattern of an EGFR inhibitor p-toluenesulfonate salt present in the form of a crystal form B.
Figure 4:
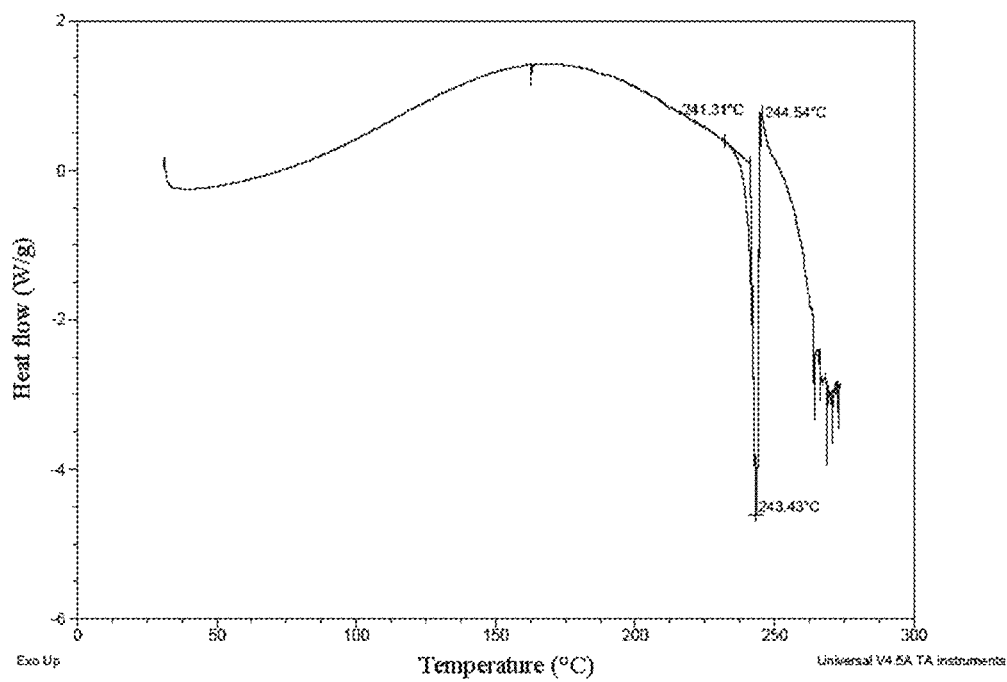
FIG. 4 is a DSC plot of the EGFR inhibitor p-toluenesulfonate salt present in the form of the crystal form B.

As tested, the solid obtained in the present example was an EGFR inhibitor p-toluenesulfonate salt, and the crystal form thereof was named as crystal form B. The XRPD data of the crystal form was as shown in Table 2, the XRPD pattern was as shown in FIG. 3, and the DSC plot was as shown in FIG. 4.

TABLE 2

XRPD data of the EGFR inhibitor p-toluenesulfonate salt (crystal form B)

| Serial no. | 2θ | d-spacing | Intensity (%) |
|---|---|---|---|
| 1 | 5.79 | 15.26 | 1.23 |
| 2 | 7.80 | 11.34 | 24.21 |
| 3 | 10.20 | 8.68 | 29.56 |
| 4 | 10.59 | 8.35 | 43.44 |
| 5 | 11.16 | 7.93 | 19.76 |
| 6 | 11.66 | 7.59 | 17.11 |
| 7 | 12.86 | 6.88 | 22.47 |
| 8 | 14.19 | 6.24 | 14.12 |
| 9 | 15.05 | 5.89 | 59.89 |
| 10 | 16.13 | 5.50 | 15.58 |
| 11 | 16.53 | 5.36 | 15.01 |
| 12 | 18.07 | 4.91 | 76.97 |
| 13 | 18.72 | 4.74 | 28.20 |
| 14 | 19.74 | 4.50 | 13.66 |
| 15 | 20.22 | 4.39 | 9.47 |
| 16 | 20.98 | 4.23 | 21.78 |
| 17 | 21.38 | 4.16 | 24.22 |
| 18 | 22.39 | 3.97 | 100.00 |
| 19 | 23.20 | 3.83 | 16.51 |
| 20 | 23.73 | 3.75 | 21.26 |
| 21 | 24.30 | 3.66 | 12.83 |
| 22 | 24.76 | 3.60 | 49.28 |
| 23 | 25.64 | 3.47 | 5.03 |
| 24 | 26.33 | 3.39 | 9.07 |
| 25 | 26.87 | 3.32 | 19.40 |
| 26 | 28.03 | 3.18 | 11.96 |
| 27 | 28.76 | 3.10 | 9.22 |
| 28 | 29.51 | 3.03 | 10.65 |
| 29 | 30.11 | 2.97 | 1.72 |
| 30 | 30.58 | 2.92 | 7.22 |
| 31 | 31.21 | 2.87 | 3.99 |
| 32 | 31.64 | 2.83 | 3.60 |
| 33 | 32.14 | 2.78 | 3.96 |
| 34 | 32.39 | 2.76 | 4.83 |
| 35 | 34.12 | 2.63 | 3.44 |
| 36 | 35.48 | 2.53 | 2.19 |
| 37 | 35.87 | 2.50 | 1.47 |
| 38 | 36.39 | 2.47 | 3.38 |
| 39 | 37.27 | 2.41 | 2.06 |
| 40 | 38.38 | 2.35 | 0.67 |
| 41 | 38.77 | 2.32 | 1.04 |
| 42 | 39.68 | 2.27 | 2.75 |
| 43 | 40.59 | 2.22 | 1.15 |
| 44 | 41.17 | 2.19 | 2.07 |
| 45 | 42.07 | 2.15 | 2.01 |
| 46 | 43.01 | 2.10 | 1.40 |

Example 3: EGFR Inhibitor Phosphate Salt (Crystal Form C)

At room temperature, the EGFR inhibitor present in a free base form (3.0 g, 6 mmol) was weighed, placed in a 250 mL flask, and 9 mL ethanol was added. An 85 wt % aqueous phosphoric acid solution (0.69 g, 6 mmol in terms of phosphoric acid) was added, and was stirred for 2 hours to dissolve. Then 60 mL acetone was added dropwise, and a grey solid precipitated. The mixture was filtered with suction, and the filter cake was rinsed with a small amount of acetone, oven-dried to obtain a tan solid (3.5 g, purity: 97.9%, moisture: 1.07%, melting point: 182.5 to 184.8° C.).

Figure 22:
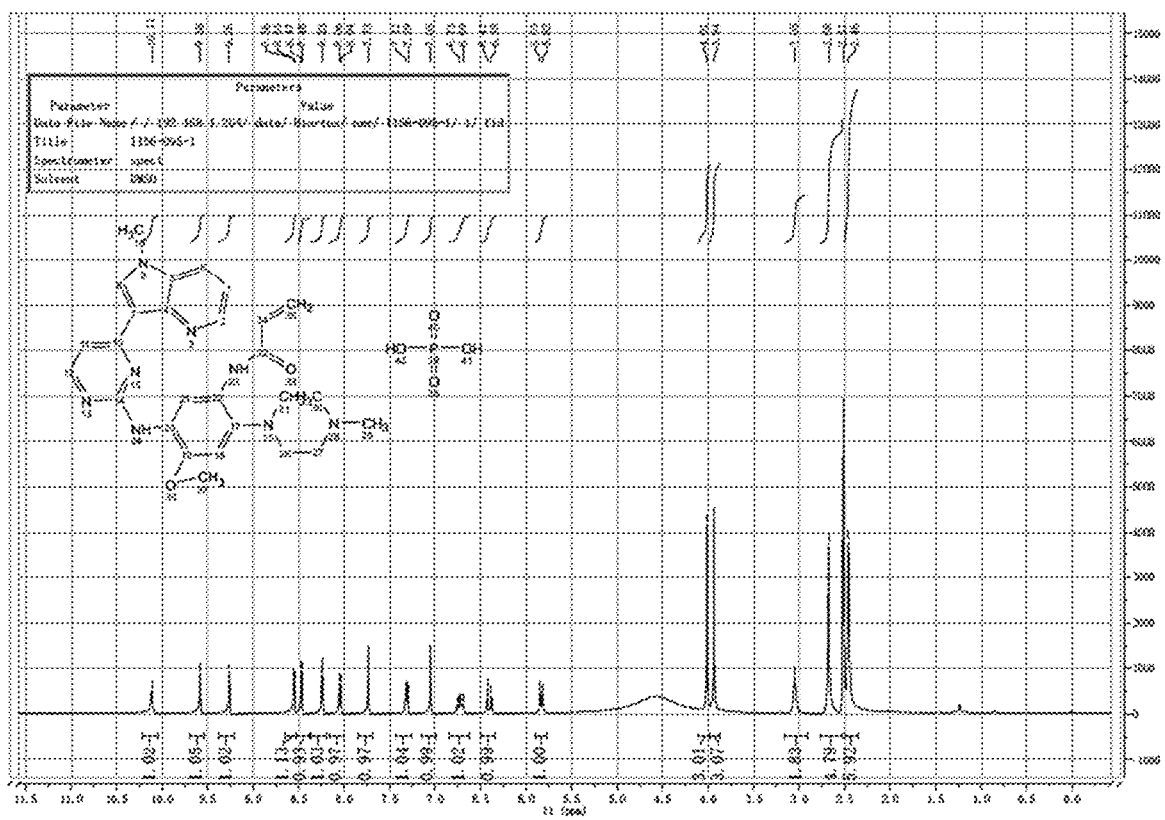
FIG. 22 is a $^1$H-NMR spectrum of the EGFR inhibitor phosphate salt present in the form of the crystal form C.

The structure confirmation data of the above product was as follows:

$^1$H-NMR (400 MHz, DMSO-d$_6$): δ10.11 (1H, s), 9.60 (1H, s), 9.27 (1H, s), 8.56 to 8.54 (1H, d), 8.47 to 8.46 (1H, d), 8.24 to 8.23 (1H, d), 8.05 to 8.03 (1H, d), 7.73 (1H, s), 7.32 to 7.29 (1H, in), 7.06 (1H, s), 6.69 to 6.64 (1H, dd), 6.42 to 6.38 (1H, d), 5.85 to 5.82 (1H, dd), 4.02 (3H, s), 3.94 (3H, s), 3.04 to 3.01 (2H, m), 2.69 (3H, s), 2.64 (2H, s), 2.42 (6H, s) (as shown in FIG. 22);

ESI-MS: m/z 501.2 [M+H]$^+$, 251.2 [M+2H]$^{2+}$.

Figure 5:
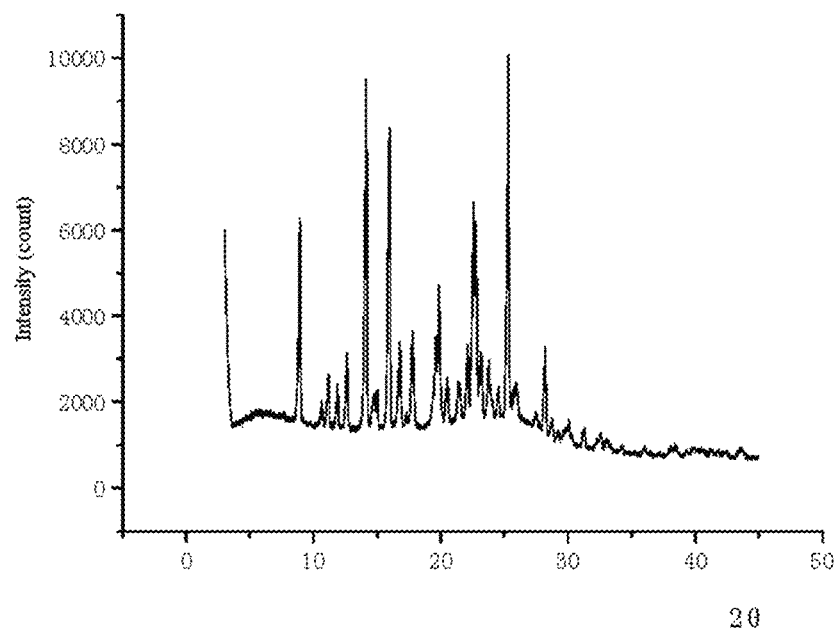
FIG. 5 is a XRPD pattern of an EGFR inhibitor phosphate salt present in the form of a crystal form C.
Figure 6:
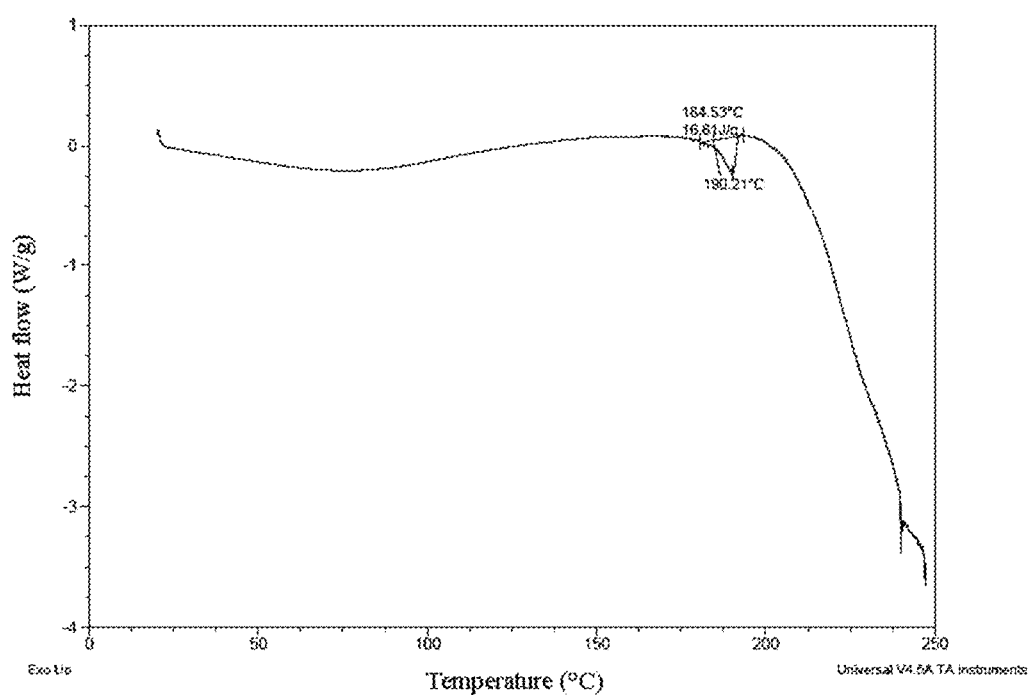
FIG. 6 is a DSC plot of the EGFR inhibitor phosphate salt present in the form of the crystal form C.

As tested, the solid obtained in the present example was an EGFR inhibitor phosphate salt, and the crystal form thereof was named as crystal form C. The XRPD data of the crystal form was as shown in Table 3, the XRPD pattern was as shown in FIG. 5, and the DSC plot was as shown in FIG. 6.

TABLE 3

XRPD data of the EGFR inhibitor phosphate salt (crystal form C)

| Serial no. | 2θ | d-spacing | Intensity (%) |
|---|---|---|---|
| 1 | 5.56 | 15.90 | 1.87 |
| 2 | 8.88 | 9.96 | 46.45 |
| 3 | 10.64 | 8.31 | 6.40 |
| 4 | 11.16 | 7.93 | 14.38 |
| 5 | 11.88 | 7.45 | 11.42 |
| 6 | 12.60 | 7.02 | 18.73 |
| 7 | 14.13 | 6.27 | 98.91 |
| 8 | 14.75 | 6.01 | 9.15 |
| 9 | 14.94 | 5.93 | 8.01 |
| 10 | 15.96 | 5.55 | 86.78 |
| 11 | 16.78 | 5.28 | 25.83 |
| 12 | 17.78 | 4.99 | 28.73 |
| 13 | 19.88 | 4.47 | 41.71 |
| 14 | 20.52 | 4.33 | 16.18 |
| 15 | 21.41 | 4.15 | 15.77 |
| 16 | 22.06 | 4.03 | 21.45 |
| 17 | 22.66 | 3.92 | 45.13 |
| 18 | 23.17 | 3.84 | 24.48 |
| 19 | 23.77 | 3.74 | 22.80 |
| 20 | 24.53 | 3.63 | 15.12 |
| 21 | 25.30 | 3.52 | 100.00 |
| 22 | 25.96 | 3.43 | 16.62 |
| 23 | 27.50 | 3.24 | 8.75 |
| 24 | 28.21 | 3.16 | 26.42 |
| 25 | 28.71 | 3.11 | 6.55 |
| 26 | 30.02 | 2.98 | 6.52 |
| 27 | 31.28 | 2.86 | 5.93 |
| 28 | 32.55 | 2.75 | 4.17 |
| 29 | 33.00 | 2.71 | 3.15 |
| 30 | 34.27 | 2.62 | 1.76 |
| 31 | 36.01 | 2.49 | 2.08 |
| 32 | 38.07 | 2.36 | 2.15 |
| 33 | 38.46 | 2.34 | 2.86 |
| 34 | 39.30 | 2.29 | 1.38 |
| 35 | 39.88 | 2.26 | 2.36 |
| 36 | 41.29 | 2.19 | 1.79 |
| 37 | 42.37 | 2.13 | 1.49 |
| 38 | 43.55 | 2.08 | 2.49 |

Example 4: EGFR Inhibitor Phosphate Salt (Amorphous)

At room temperature, the EGFR inhibitor present in a free base form (9.0 g, 18 mmol) was weighed, and placed in a 500 mL flask. An 85 wt % aqueous phosphoric acid solution (2.08 g, 18 mmol in terms of phosphoric acid) was added, and was stirred at 40 to 50° C. to dissolve. Then 180 mL acetone was added dropwise, and a grey solid precipitated. The mixture was filtered with suction, and the filter cake was rinsed with a small amount of acetone, oven-dried to obtain a light grey solid (11.0 g, purity: 98.5%).

The structure confirmation data of the above product was as follows:

ESI-MS: m/z 501.2 [M+H]$^+$, 251.2 [M+2H]$^{2+}$.

Figure 7:
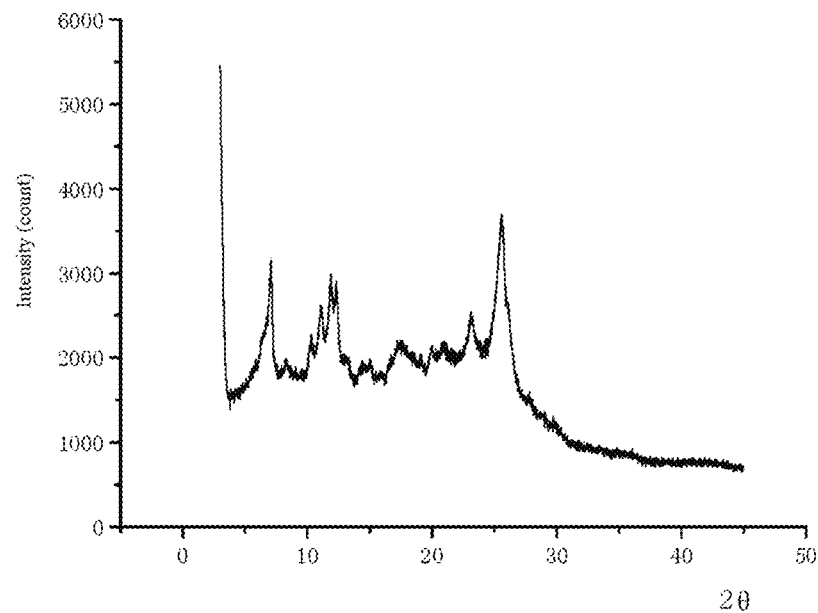
FIG. 7 is a XRPD pattern of an EGFR inhibitor phosphate salt present in an amorphous form.

As tested, the solid obtained in the present example was amorphous powder of an EGFR inhibitor phosphate salt, and the XRPD pattern thereof was as shown in FIG. 7.

Example 5: EGFR Inhibitor Hydrochloride Salt (Crystal Form D)

At room temperature, the EGFR inhibitor present in a free base form (15.0 g, 30 mmol) was weighed, and placed in a 500 mL flask. An ethanol (45 mL) solution of concentrated hydrochloric acid (2.5 mL, 30 mmol in terms of hydrogen chloride) was added, and was stirred at 40 to 50° C. to dissolve. Then 360 mL acetone was added dropwise, and a grey solid precipitated. The mixture was filtered with suction, and the filter cake was rinsed with a small amount of acetone, oven-dried to obtain a tan solid (15 g, purity: 99.2%, moisture: 0.77%, melting point: 250.5° C. to 152.8° C.).

Figure 23:
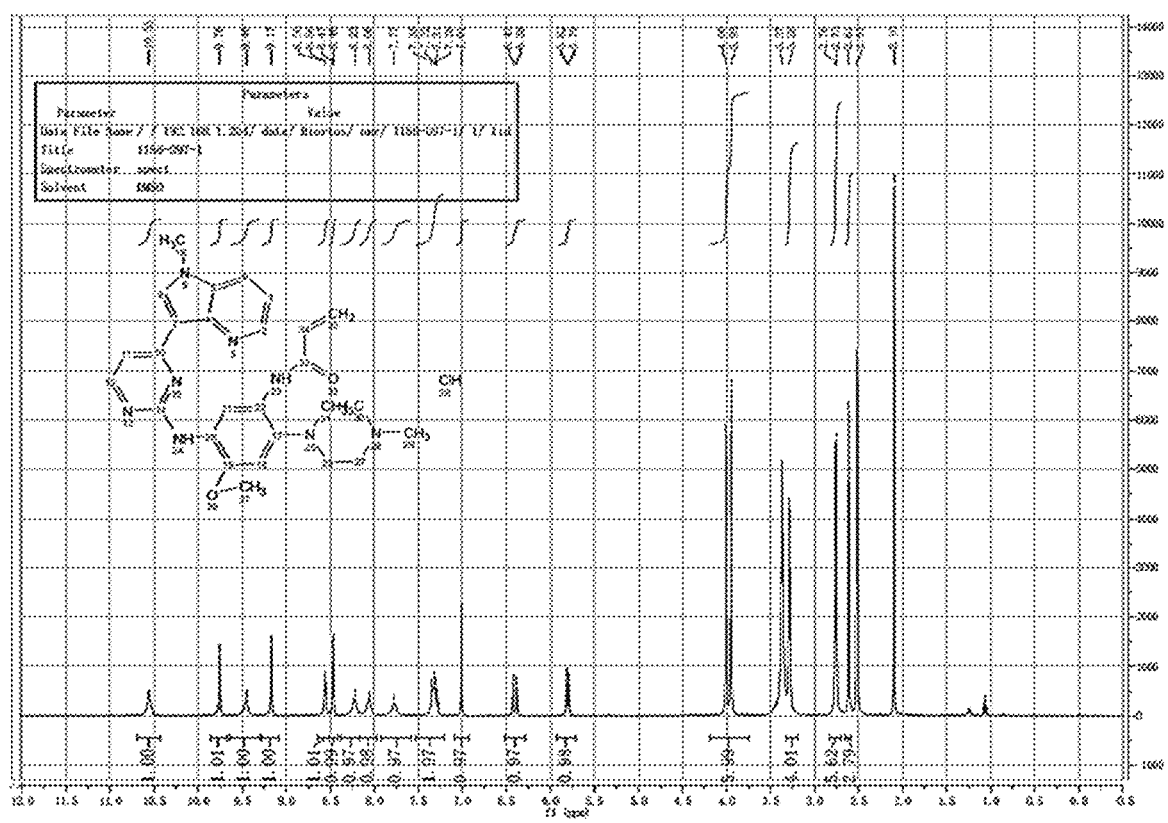
FIG. 23 is a $^1$H-NMR spectrum of the EGFR inhibitor hydrochloride salt present in the form of the crystal form D.

The structure confirmation data of the above product was as follows:

$^1$H-NMR (400 MHz, DMSO-d$_6$): δ10.55 (1H, s), 9.76 (1H, s), 9.46 (1H, s), 9.17 (1H, s), 8.56 to 8.55 (1H, d), 8.47 to 8.46 (1H, d), 8.23 (1H, s), 8.06 (1H, s), 7.77 (1H, s), 7.35 to 7.28 (2H, d), 7.01 (1H, s), 6.62 to 6.38 (1H, dd), 5.82 to 5.79 (1H, d), 4.00 (3H, s), 3.95 (3H, s), 3.28 (4H, s), 2.76 to 2.75 (6H, s), 2.61 (3H, s) (as shown in FIG. 23);

ESI-MS: m/z 501.2 [M+H]$^+$, 251.2 [M+2H]$^{2+}$.

Figure 8:
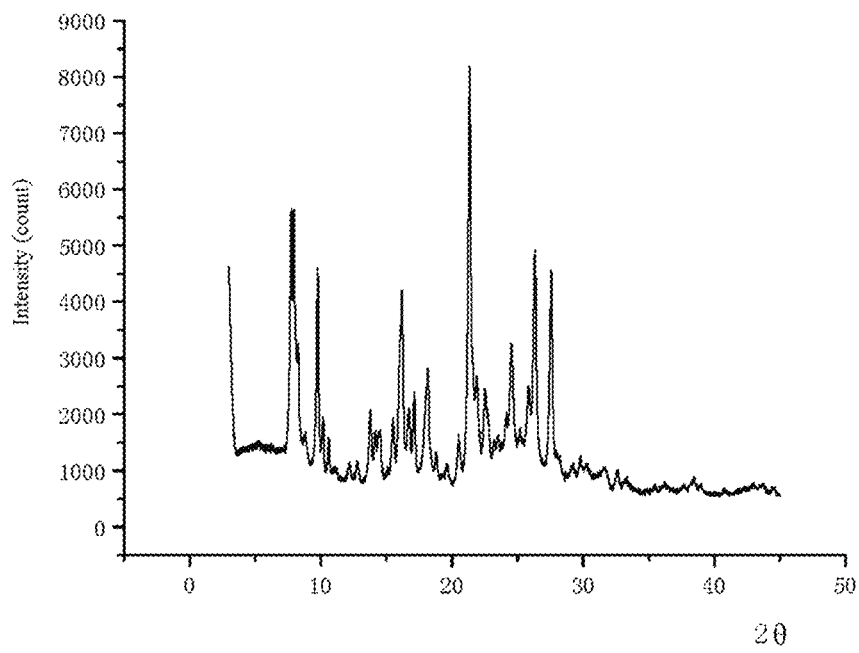
FIG. 8 is a XRPD pattern of an EGFR inhibitor hydrochloride salt present in the form of a crystal form D.
Figure 9:
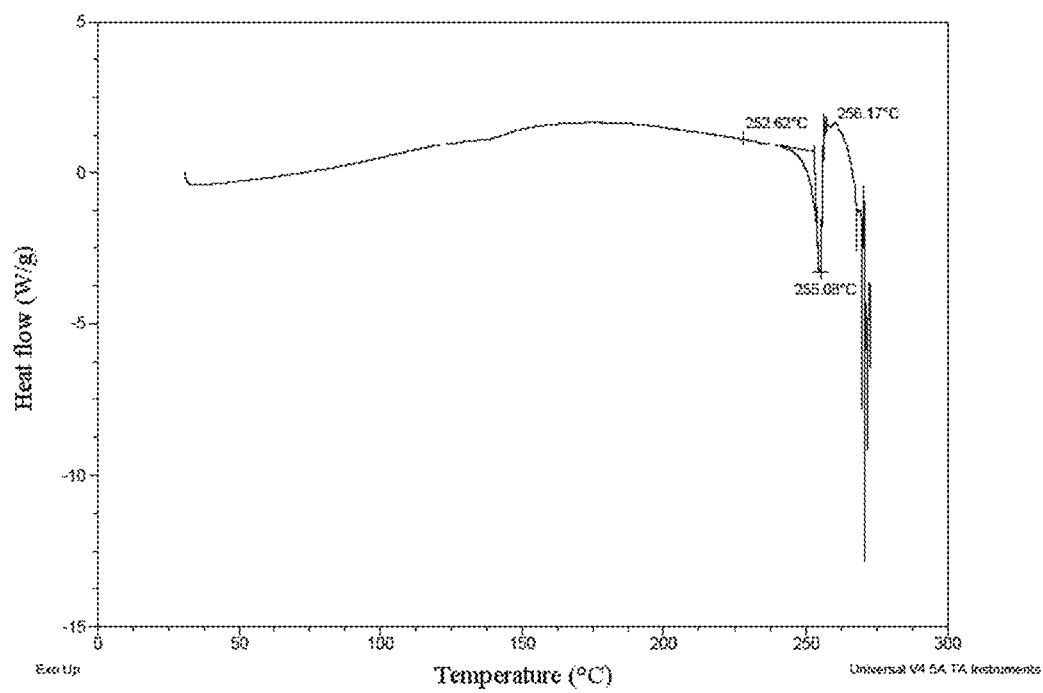
FIG. 9 is a DSC plot of the EGFR inhibitor hydrochloride salt present in the form of the crystal form D.

As tested, the solid obtained in the present example was an EGFR inhibitor hydrochloride salt, and the crystal form thereof was named as crystal form D. The XRPD data of the crystal form was as shown in Table 4, the XRPD pattern was as shown in FIG. 8, and the DSC plot was as shown in FIG. 9.

TABLE 4

XRPD data of the EGFR inhibitor hydrochloride salt (crystal form D)

| Serial no. | 2θ | d-spacing | Intensity (%) |
|---|---|---|---|
| 1 | 5.28 | 16.74 | 2.54 |
| 2 | 7.82 | 11.31 | 50.15 |
| 3 | 8.82 | 10.04 | 7.91 |
| 4 | 9.77 | 9.06 | 48.34 |
| 5 | 10.60 | 8.34 | 8.18 |
| 6 | 12.18 | 7.27 | 3.59 |
| 7 | 12.79 | 6.92 | 4.27 |
| 8 | 13.77 | 6.43 | 16.69 |
| 9 | 14.52 | 6.10 | 11.75 |
| 10 | 15.51 | 5.71 | 14.41 |
| 11 | 15.99 | 5.54 | 30.49 |
| 12 | 16.21 | 5.47 | 44.59 |
| 13 | 16.73 | 5.30 | 17.41 |
| 14 | 17.13 | 5.18 | 21.36 |
| 15 | 18.18 | 4.88 | 27.33 |
| 16 | 18.81 | 4.72 | 6.89 |
| 17 | 19.62 | 4.53 | 4.40 |
| 18 | 20.51 | 4.33 | 11.17 |
| 19 | 21.34 | 4.16 | 100.00 |
| 20 | 21.90 | 4.06 | 25.67 |
| 21 | 22.52 | 3.95 | 22.26 |
| 22 | 23.50 | 3.79 | 11.64 |
| 23 | 24.56 | 3.62 | 34.56 |
| 24 | 25.85 | 3.45 | 23.64 |
| 25 | 26.34 | 3.38 | 56.68 |
| 26 | 27.57 | 3.26 | 51.23 |
| 27 | 29.23 | 3.06 | 5.97 |
| 28 | 29.79 | 3.00 | 7.48 |
| 29 | 30.27 | 2.95 | 5.95 |
| 30 | 31.58 | 2.83 | 5.36 |
| 31 | 32.61 | 2.75 | 4.80 |
| 32 | 33.25 | 2.69 | 2.64 |
| 33 | 35.45 | 2.53 | 1.26 |
| 34 | 36.17 | 2.48 | 2.18 |
| 35 | 37.65 | 2.39 | 1.90 |
| 36 | 38.46 | 2.34 | 3.29 |
| 37 | 40.80 | 2.21 | 0.91 |
| 38 | 42.95 | 2.11 | 2.38 |
| 39 | 43.73 | 2.07 | 2.18 |
| 40 | 44.59 | 2.03 | 1.45 |

Example 6: EGFR Inhibitor Citrate Salt (Crystal Form E)

At room temperature, the EGFR inhibitor present in a free base form (10.0 g, 20 mmol) was weighed, placed in a 500 mL flask, and 30 mL ethanol was added. Citric acid monohydrate (4.2 g, 20 mmol) was added, and was stirred at 40 to 50° C. to dissolve. Then 200 mL acetone was added dropwise, and a grey solid precipitated. The mixture was filtered with suction, and the filter cake was rinsed with a small amount of acetone, oven-dried to obtain a light grey solid (11.3 g, purity: 98.9%, moisture: 0.97%, melting point: 193.1 to 195.6° C.).

Figure 24:
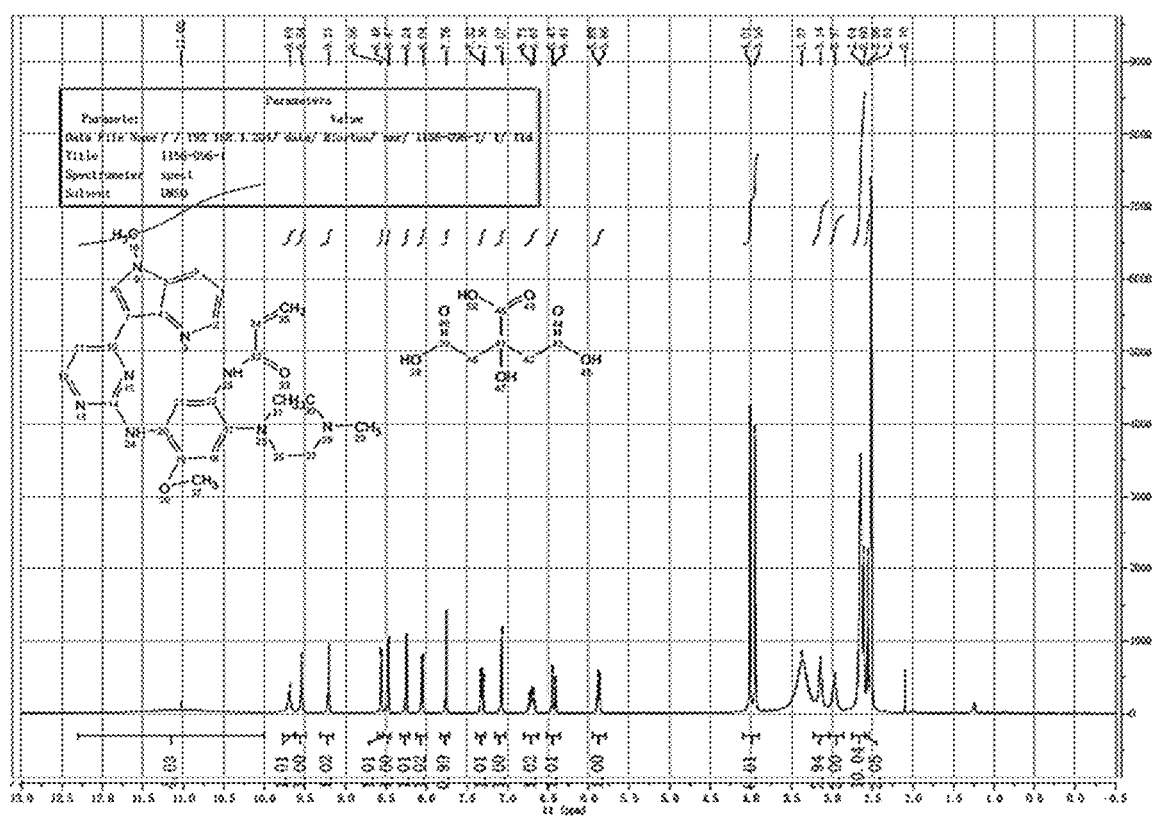
FIG. 24 is a $^1$H-NMR spectrum of the EGFR inhibitor citrate salt present in the form of the crystal form E.

The structure confirmation data of the above product was as follows:

$^1$H-NMR (400 MHz, DMSO-d$_6$): δ11.5 to 10.5 (4H, s), 9.68 (1H, s), 9.54 (1H, s), 9.20 (1H, s), 8.56 to 8.55 (1H, d), 8.48 to 8.47 (1H, d), 8.24 to 8.23 (1H, d), 7.75 (1H, s), 7.32 to 7.30 (1H, d), 7.07 (1H, s), 6.69 to 6.67 (1H, dd), 6.44 to 6.40 (1H, d), 5.89 to 5.86 (1H, d), 4.01 (3H, s), 3.95 (3H, s), 3.13 (3H, m), 2.95 (2H, s), 2.64 to 2.59 (10H, s), 2.57 (2H, s) (as shown in FIG. 24);

ESI-MS: m/z 501.2 [M+H]$^+$, 251.2 [M+2H]$^{2+}$.

As tested, the solid obtained in the present example was an EGFR inhibitor citrate salt, and the crystal form thereof was named as crystal form E. The XRPD data of the crystal form was as shown in Table 5, the XRPD pattern was as shown in FIG. 10, and the DSC plot was as shown in FIG. 11.

TABLE 5

XRPD data of the EGFR inhibitor citrate salt (crystal form E)

| Serial no. | 2θ | d-spacing | Intensity (%) |
|---|---|---|---|
| 1 | 5.40 | 16.37 | 100.00 |
| 2 | 7.69 | 11.50 | 2.04 |
| 3 | 9.00 | 9.82 | 16.27 |
| 4 | 10.80 | 8.19 | 21.34 |
| 5 | 11.99 | 7.38 | 61.71 |
| 6 | 12.39 | 7.14 | 16.17 |
| 7 | 13.35 | 6.63 | 15.06 |
| 8 | 14.71 | 6.02 | 0.71 |

TABLE 5-continued

XRPD data of the EGFR inhibitor citrate salt (crystal form E)

| Serial no. | 2θ | d-spacing | Intensity (%) |
|---|---|---|---|
| 9 | 15.95 | 5.56 | 14.40 |
| 10 | 16.58 | 5.35 | 9.23 |
| 11 | 17.47 | 5.08 | 24.39 |
| 12 | 18.19 | 4.88 | 6.90 |
| 13 | 19.28 | 4.60 | 6.08 |
| 14 | 20.37 | 4.36 | 10.15 |
| 15 | 21.21 | 4.19 | 29.45 |
| 16 | 23.44 | 3.80 | 4.91 |
| 17 | 24.88 | 3.58 | 28.55 |
| 18 | 25.36 | 3.51 | 21.74 |
| 19 | 26.75 | 3.33 | 4.98 |
| 20 | 27.77 | 3.21 | 3.24 |
| 21 | 28.92 | 3.09 | 6.73 |
| 22 | 31.27 | 2.86 | 3.23 |
| 23 | 33.88 | 2.65 | 2.55 |
| 24 | 35.98 | 2.50 | 0.30 |
| 25 | 39.51 | 2.28 | 0.63 |
| 26 | 41.62 | 2.17 | 1.39 |
| 27 | 43.59 | 2.08 | 0.69 |

Example 7: Hygroscopicity Study of Crystal Forms

Hygroscopicity comparison study was carried out for various pharmaceutically acceptable salts of EGFR inhibitor present in the form of crystal in Examples 1 to 3 and 5 to 6, the amorphous EGFR inhibitor phosphate salt in Example 4, and the EGFR inhibitor present in a free base form. Tests were conducted according to the method in the Pharmacopoeia of the People's Republic of China, 2015 edition, part 4, appendix 9103 (temperature: 25° C.±1° C., relative humidity: 80%±2%), and the results were as shown in Table 6.

TABLE 6

Hygroscopicity study of various pharmaceutically acceptable salts of EGFR inhibitor

| Type | Weight gain over 6 hours (%) | Weight gain over 24 hours (%) | Hygroscopicity |
|---|---|---|---|
| free base | 1.7 | 2.2 | hygroscopic |
| mesylate salt | 6.86 | 10.64 | hygroscopic |
| p-toluenesulfonate salt | 0.04 | 0.04 | almost non-hygroscopic |
| phosphate salt (crystal form C) | 9.15 | 11.98 | hygroscopic |
| phosphate salt (amorphous) | 1.2 | 1.5 | slightly hygroscopic |
| hydrochloride salt | 0.72 | 1.29 | slightly hygroscopic |
| citrate salt | 2.23 | 2.48 | hygroscopic |

As demonstrated by the results, under the condition of 25° C./RH 80%, among the six crystal forms of the pharmaceutically acceptable salts of EGFR inhibitor of the present disclosure, the p-toluenesulfonate salt crystal form B, hydrochloride salt crystal form D and amorphous phosphate salt all had a lower hygroscopicity, and the citrate salt crystal form E had a comparable hygroscopicity, while the mesylate salt crystal form A and phosphate salt crystal form C had a higher hygroscopicity, as compared with that of the EGFR inhibitor present in a free base form.

With regard to the description of hygroscopic properties and definition of hygroscopic weight gain, refer to the Pharmacopoeia of the People's Republic of China, 2015 edition, part 4, appendix 9103, experimental guideline of drug hygroscopicity, herein descried by way of example as follows.

Deliquescence: absorb enough water to form a liquid.

Very hygroscopic: hygroscopic weight gain less than 15%.

Hygroscopic: hygroscopic weight gain less than 15% but not less than 2%.

Slightly hygroscopic: hygroscopic weight gain less than 2% but not less than 0.2%.

Non- or almost non-hygroscopic: hygroscopic weight gain less than 0.2%.

Example 8: Solubility Study of Crystal Forms

Various pharmaceutically acceptable salts of EGFR inhibitor present in form of crystal in Examples 1 to 3 and 5 to 6 were classified with reference to the relevant requirements of the Pharmacopoeia of the People's Republic of China and the Bio-pharmaceutics Classification System (BCS).

(a) Relevant Requirements of Solubility in the Pharmacopoeia of the People's Republic of China, 2015 Edition, General Notices:

TABLE 7

Relevant requirements of solubility in general notices of the Pharmacopoeia of the People's Republic of China

| Definition | The amount of solvent required to dissolve 1 g solute (ml) | Solubility range (mg/ml) |
|---|---|---|
| Very soluble (vs) | <1 | ≥1000 |
| Freely soluble (fs) | 1 to less than 10 | 100 to 1000 |
| Soluble (s) | 10 to less than 30 | 33 to 100 |
| Sparingly soluble (sps) | 30 to less than 100 | 10 to 33 |
| Slightly soluble (ss) | 100 to less than 1000 | 1 to 10 |
| Very slightly soluble (vss) | 1000 to less than 10000 | 0.1 to 1 |
| Practically insoluble or insoluble (pi) | ≥10000 | <0.1 |

(b) Relevant Requirements of Solubility in BCS:

$$Do=(Mo/Vo)/Cs;$$

wherein Do: dose index; Mo: highest single dose of the drug (with reference to the relevant dose of osimertinib, tentatively set to 80 mg); Vo: volume of body fluid required for dissolving the drug (about 250 ml); Cs: saturated solubility of the drug;

if Do≤1, solubility is high; and if Do>1, solubility is low.

(c) Experimental Process and Results:

Using an EGFR inhibitor free base as a control, linear regression was carried out by plotting peak area versus concentration, and the corresponding linear equation was obtained in the range of 0.025 to 1.5 mg/ml: A=19775.0411c+2.4256, r=1.0000.

Water was used as solvent. An appropriate amount of the EGFR inhibitor mesylate salt, p-toluenesulfonate salt, phosphate salt, hydrochloride salt and citrate salt prepared in Examples 1 to 3 and 5 to 6 was weighed, and prepared into saturated solutions. Samples were taken after standing for 1 hour, 4 hours, and 24 hours, respectively, and the concentration of each sample in saturation state was calculated according to the linear equation. The results were as shown in Table 8.

TABLE 8

Solubility classification results of various pharmaceutically acceptable salts of EGFR inhibitor in water

| Type | 1 h (mg/ml) | 4 h (mg/ml) | 24 h (mg/ml) | Pharmacopoeia of the People's Republic of China Solubility level | BCS level (Do) |
|---|---|---|---|---|---|
| mesylate salt | 223.02 | 224.00 | 255.75 | freely soluble | 0.0013 < 1 |
| p-toluenesulfonate salt | 1.82 | 1.78 | 1.56 | slightly soluble | 0.2057 < 1 |
| phosphate salt (crystal form C) | 107.15 | 133.32 | 137.13 | freely soluble | 0.0023 < 1 |
| phosphate salt (amorphous) | 88.32 | 92.14 | 94.56 | freely soluble | 0.0034 < 1 |
| hydrochloride salt | 13.43 | 11.09 | 10.59 | sparingly soluble | 0.0302 < 1 |
| citrate salt | 143.59 | 137.34 | 133.57 | freely soluble | 0.0024 < 1 |
| free base | <0.025 | <0.025 | <0.025 | practically insoluble or insoluble | 606.30 > 1 |

Artificial gastric fluid was used as solvent. An appropriate amount of the EGFR inhibitor mesylate salt (crystal form A), p-toluenesulfonate salt (crystal form B), phosphate salt (crystal form C), phosphate salt (amorphous), hydrochloride salt (crystal form C), and citrate salt (crystal form E) prepared in Examples 1 to 6 was weighed, and prepared into saturated solutions. Samples were taken after standing for 1 hour, 4 hours, and 24 hours, respectively, and the concentration of each sample in saturation state was calculated according to the linear equation. The results were as shown in Table 9.

TABLE 9

Solubility classification results of various pharmaceutically acceptable salts of EGFR inhibitor in artificial gastric fluid

| Type | 1 h (mg/ml) | 4 h (mg/ml) | 24 h (mg/ml) | Pharmacopoeia of the People's Republic of China Solubility level | BCS level (Do) |
|---|---|---|---|---|---|
| mesylate salt | 248.77 | 370.37 | 379.12 | freely soluble | 0.0008 < 1 |
| p-toluenesulfonate salt | 46.21 | 46.75 | 47.03 | soluble | 0.0068 < 1 |
| phosphate salt (crystal form C) | 156.70 | 159.14 | 147.08 | freely soluble | 0.0022 < 1 |
| phosphate salt (amorphous) | 123.56 | 136.76 | 138.91 | freely soluble | 0.0023 < 1 |
| hydrochloride salt | 83.79 | 79.18 | 70.03 | soluble | 0.0046 < 1 |
| citrate salt | 168.51 | 196.47 | 176.88 | freely soluble | 0.0018 < 1 |
| free base | 0.84 | 0.86 | 0.71 | very slightly soluble | 0.4515 < 1 |

(d) Result:

The six pharmaceutically acceptable salts, i.e., the EGFR inhibitor mesylate salt, p-toluenesulfonate salt, phosphate salt (crystal form C), phosphate salt (amorphous), hydrochloride salt and citrate salt prepared in the present disclosure and the EGFR inhibitor free base had higher solubility in artificial gastric fluid than in water, and no significant degradation occurred. In addition, whether in water or in artificial gastric fluid, the solubility of the pharmaceutically acceptable salts prepared in the present disclosure was much higher than that of the free base, and salt formation might improve the low solubility of free base. According to the BCS solubility standard, five pharmaceutically acceptable salts had a Do value less than 1 in water and artificial gastric fluid. The solubility of the EGFR inhibitor mesylate salt, phosphate salt (crystal form C), phosphate salt (amorphous) and citrate salt in water and artificial gastric fluid was high, with reference to solubility classification in the Pharmacopoeia of the People's Republic of China, 2015 edition, general notices.

Example 11: Stability Study of Crystal Forms

Figure 12:
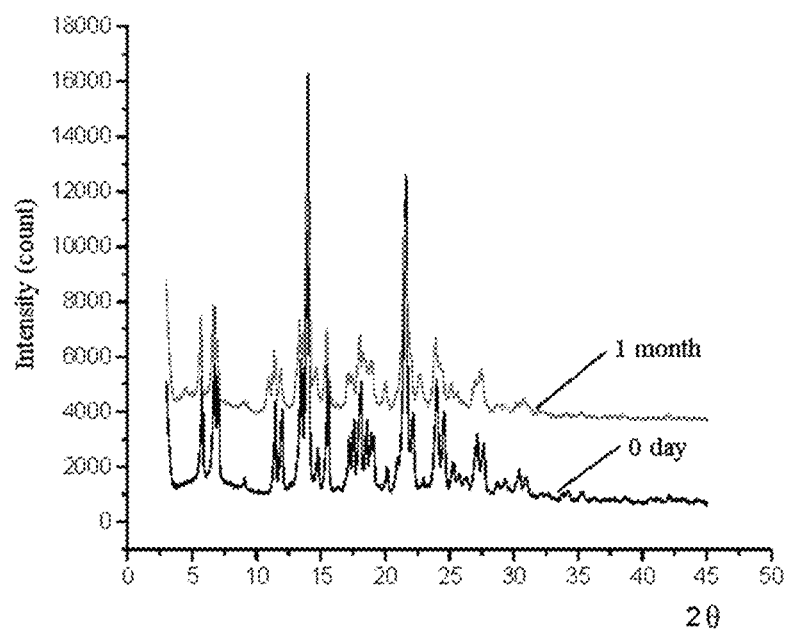
FIG. 12 is the stability test result of the EGFR inhibitor mesylate salt present in the crystal form A (XRPD comparison graph), wherein the XRPD pattern of the sample determined at the start time and the XRPD pattern of the sample determined after standing for 1 month at 40° C./75% RH are in bottom-to-top order.
Figure 13:
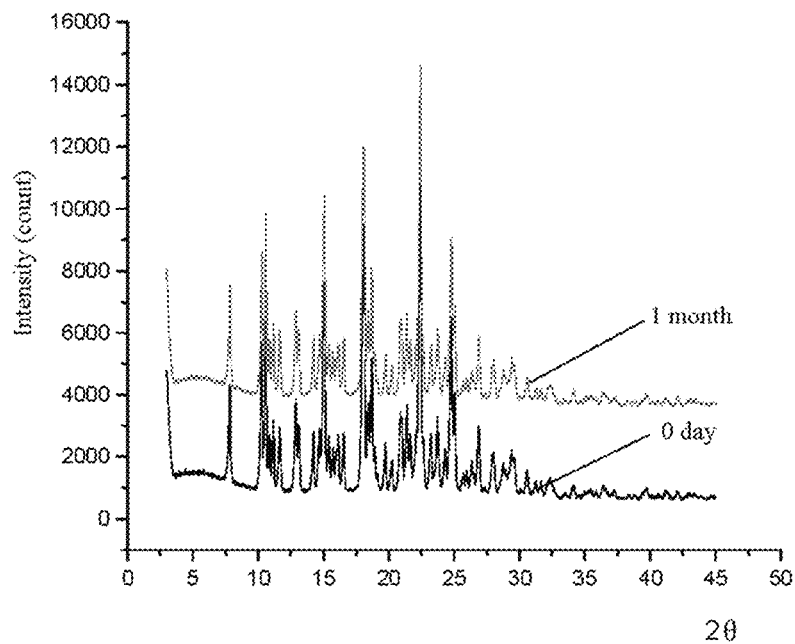
FIG. 13 is the stability test result of the EGFR inhibitor p-toluenesulfonate salt present in the form of the crystal form B (XRPD comparison graph), wherein the XRPD pattern of the sample determined at the start time and the XRPD pattern of the sample determined after standing for 1 month at 40° C./75% RH are in bottom-to-top order.
Figure 14:
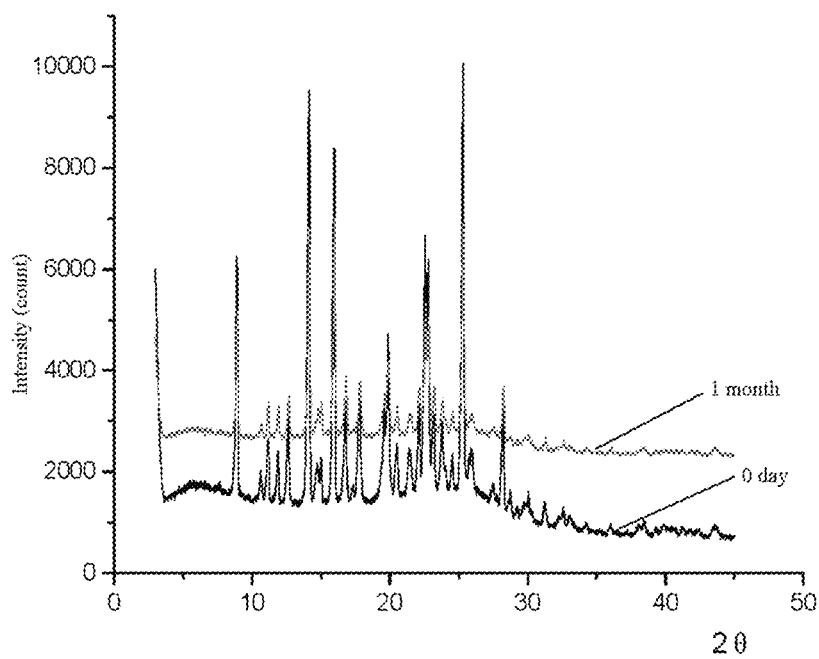
FIG. 14 is the stability test result of the EGFR inhibitor phosphate salt present in the crystal form C (XRPD comparison graph), wherein the XRPD pattern of the sample determined at the start time and the XRPD pattern of the sample determined after standing for 1 month at 40° C./75% RH are in bottom-to-top order.
Figure 15:
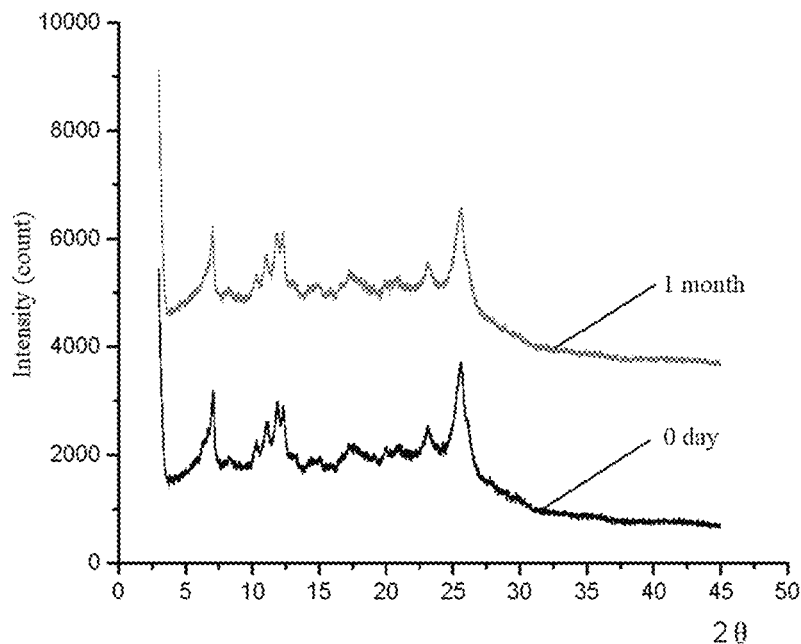
FIG. 15 is the stability test result of the EGFR inhibitor phosphate salt present in the amorphous form (XRPD comparison graph), wherein the XRPD pattern of the sample determined at the start time and the XRPD pattern of the sample determined after standing for 1 month at 40° C./75% RH are in bottom-to-top order.
Figure 16:
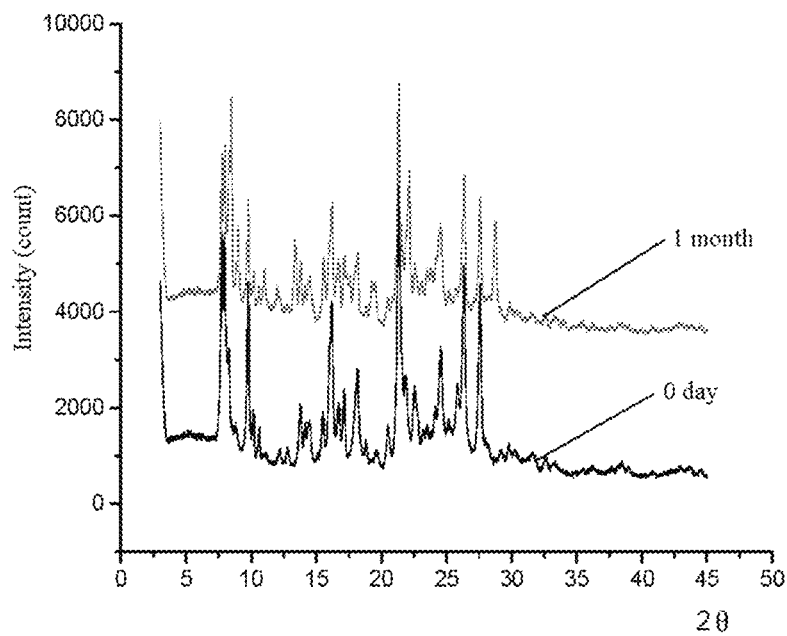
FIG. 16 is the stability test result of the EGFR inhibitor hydrochloride salt present in the form of the crystal form D (XRPD comparison graph), wherein the XRPD pattern of the sample determined at the start time and the XRPD pattern of the sample determined after standing for 1 month at 40° C./75% RH are in bottom-to-top order.
Figure 17:
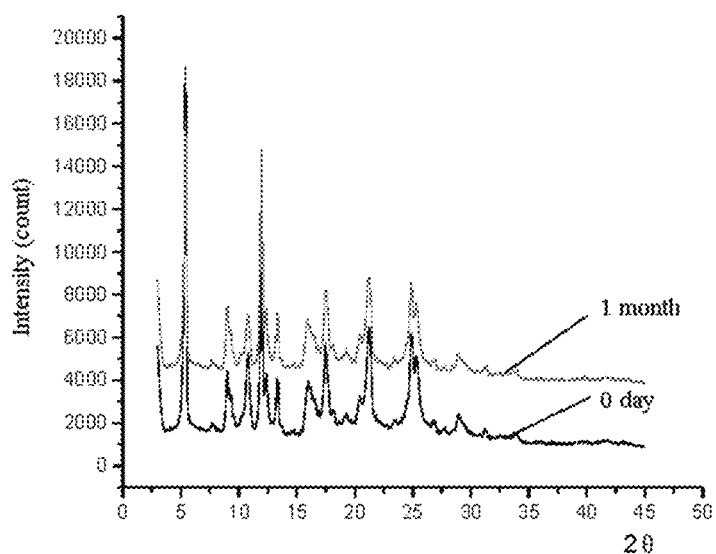
FIG. 17 is the stability test result of the EGFR inhibitor citrate salt present in the form of the crystal form E (XRPD comparison graph), wherein the XRPD pattern of the sample determined at the start time and the XRPD pattern of the sample determined after standing for 1 month at 40° C./75% RH are in bottom-to-top order.

The six pharmaceutically acceptable salts of EGFR inhibitor in Examples 1 to 6 were placed in a condition of 40° C./75% RH, and a one month accelerated stability study was carried out. Samples were taken at the end of 0 and 1 month respectively, and emphasis was placed upon the shape, purity and crystal form stability (XRPD pattern) of the samples. The results were as shown in Table 10. The stability result of the mesylate salt crystal form A was as shown in FIG. 12, the stability result of the p-toluenesulfonate salt crystal form B was as shown in FIG. 13, the stability result of the phosphate salt crystal form C was as shown in FIG. 14, the stability result of the phosphate amorphous powder was as shown in FIG. 15, the stability result of the hydrochloride salt crystal form D was as shown in FIG. 16, and the stability result of the citrate salt crystal form E was as shown in FIG. 17.

TABLE 10

Results of stability of the various pharmaceutically acceptable salts of EGFR inhibitor

| Sample name and batch no. | | Appearance | Purity (%) | XRPD pattern |
|---|---|---|---|---|
| mesylate salt | 0 month | light brown solid | 99.0 | consistent |
| (crystal form A) | 1 month | light brown solid | 99.2 | |
| p-toluenesulfonate | 0 month | light tan solid | 98.7 | consistent |
| salt (crystal form B) | 1 month | light tan solid | 98.7 | |
| phosphate salt | 0 month | tan solid | 98.5 | consistent |
| (crystal form C) | 1 month | tan solid | 98.5 | |
| phosphate salt | 0 month | light grey solid | 98.9 | consistent |
| (amorphous) | 1 month | light grey solid | 98.7 | |
| hydrochloride salt | 0 month | tan solid | 99.2 | consistent |
| (crystal form D) | 1 month | tan solid | 99.3 | |
| citrate salt | 0 month | light grey solid | 98.9 | consistent |
| (crystal form E) | 1 month | light grey solid | 99.1 | |

According to the experiment results, after standing for 1 month under the experiment condition, the six pharmaceutically acceptable salts of EGFR inhibitor of the present disclosure were all stable, without any change, demonstrating good stability. Stable refers to no occurrence of degradation and no detection of transformation to other crystal forms by analytical means such as chromatography and XRPD.

Based on the above hygroscopicity, solubility and stability study results, the pharmaceutically acceptable salts of EGFR inhibitor of the present disclosure and specific crystal forms thereof have excellent physicochemical properties, more suitable for development into drugs, and satisfy requirements for bioavailability and drug efficacy.

The above examples are merely preferred examples of the present disclosure and are not intended to limit the present disclosure. Although the present disclosure has been described in detail with reference to the foregoing examples, those skilled in the art can still modify the technical solutions described in the foregoing examples, or substitute some of the technical features with equivalents thereof. Any modification, equivalent substitution, improvement, etc. made within the spirit and scope of the present disclosure is intended to be included within the scope of protection of the present disclosure.

What is claimed is:

1. A crystal form E of a citrate salt of the EGFR inhibitor represented by formula I,

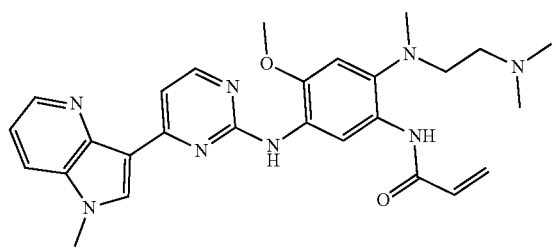

formula I wherein the X-ray powder diffraction pattern of the crystal form E has characteristic peaks at 2θ values of 5.4°±0.2°, 10.8°±0.2°, 12.0°±0.2°, 17.5°±0.2°, 21.2°±0.2°, 24.9°±0.2°, and 25.4°±0.2°.

2. A crystal form A of a mesylate salt of the EGFR inhibitor represented by formula I,

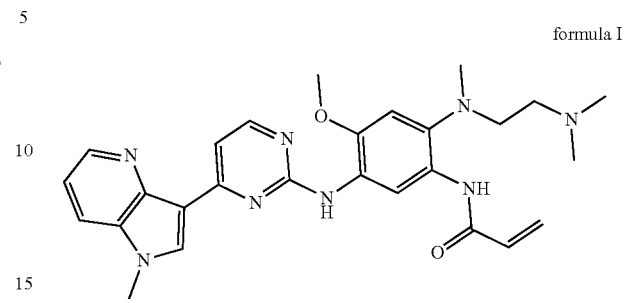

formula I wherein the X-ray powder diffraction pattern of the crystal form A has characteristic peaks at 2θ values of 6.8°±0.2°, 13.5°±0.2°, 14.0°±0.2°, 15.6°±0.2°, 18.1°±0.2°, 21.6°±0.2°, and 24.0°±0.2°.

3. A crystal form B of a p-toluenesulfonate salt of the EGFR inhibitor represented by formula I,

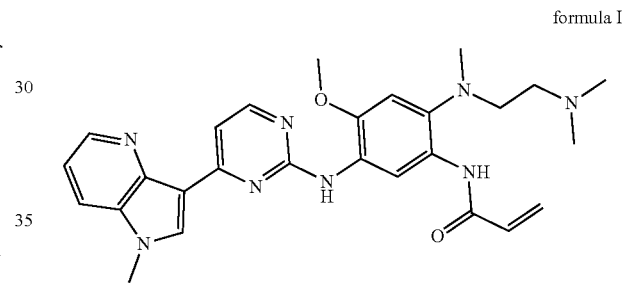

formula I wherein the X-ray powder diffraction pattern of the crystal form B has characteristic peaks at 2θ values of 10.6°±0.2°, 15.1°±0.2°, 18.1°±0.2°, 22.4°±0.2° and 24.8°±0.2°.

4. A crystal form C of a phosphate salt of the EGFR inhibitor represented by formula I,

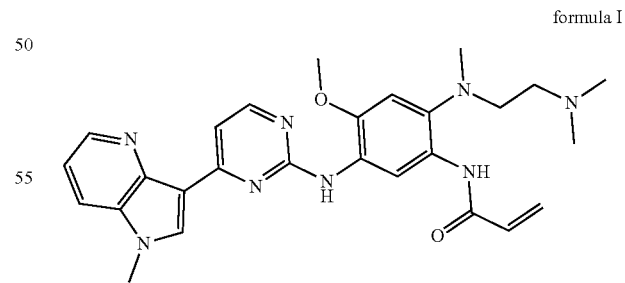

formula I wherein the X-ray powder diffraction pattern of the crystal form C has characteristic peaks at 2θ values of 8.9°±0.2°, 14.1°±0.2°, 16.0°±0.2°, 19.9°±0.2°, 22.7°±0.2°, and 25.3°±0.2°.

5. A crystal form D of a hydrochloride salt of the EGFR inhibitor represented by formula I,

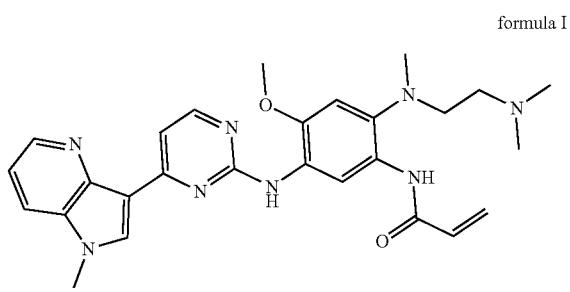 [SMILES: C=CC(=O)Nc1cc(Nc2nccc(-c3cn(C)c4cccnc34)n2)c(OC)cc1N(C)CCN(C)C]

formula I wherein the X-ray powder diffraction pattern of the crystal form D has characteristic peaks at 2θ values of 7.8°±0.2°, 9.8°±0.2°, 16.2°±0.2°, 21.3°±0.2°, 26.3°±0.2°, and 27.6°±0.2°.

6. A method of treating cancer, comprising administering to a patient in need thereof a therapeutically effective amount of the crystal form E of the EGFR inhibitor according to claim 1.

7. A method of treating cancer, comprising administering to a patient in need thereof a therapeutically effective amount of the crystal form A of the EGFR inhibitor according to claim 2.

8. A method of treating cancer, comprising administering to a patient in need thereof a therapeutically effective amount of the crystal form B of the EGFR inhibitor according to claim 3.

9. A method of treating cancer, comprising administering to a patient in need thereof a therapeutically effective amount of the crystal form C of the EGFR inhibitor according to claim 4.

10. A method of treating cancer, comprising administering to a patient in need thereof a therapeutically effective amount of the crystal form D of the EGFR inhibitor according to claim 5.

11. The crystal form E of the EGFR inhibitor according to claim 1, wherein the crystal form has an X-ray powder diffraction pattern substantially as shown in FIG. 10.

12. The crystal form A of the EGFR inhibitor according to claim 2, wherein the crystal form has an X-ray powder diffraction pattern substantially as shown in FIG. 1.

13. The crystal form B of the EGFR inhibitor according to claim 3, wherein the crystal form has an X-ray powder diffraction pattern substantially as shown in FIG. 3.

14. The crystal form C of the EGFR inhibitor according to claim 4, wherein the crystal form has an X-ray powder diffraction pattern substantially as shown in FIG. 5.

15. The crystal form D of the EGFR inhibitor according to claim 5, wherein the crystal form has an X-ray powder diffraction pattern substantially as shown in FIG. 8.

* * * * *